United States Patent
Cameron et al.

(10) Patent No.: US 11,017,882 B2
(45) Date of Patent: May 25, 2021

(54) METHOD FOR PREDICTING THE OFF-TARGET BIDING OF A PEPTIDE WHICH BINDS TO A TARGET PEPTIDE PRESENTED BY A MAJOR HISTOCOMPATIBILITY COMPLEX

(71) Applicants: IMMUNOCORE LIMITED, Abingdon Oxfordshire (GB); ADAPTIMMUNE LIMITED, Abingdon Oxfordshire (GB)

(72) Inventors: Brian John Cameron, Abingdon (GB); Annelise Brigitte Vuidepot, Abingdon (GB); Bent Karsten Jakobsen, Abingdon (GB)

(73) Assignees: Immunocore Limited, Abingdon Oxfordshire (GB); Adaptimmune Limited, Abingdon Oxfordshire (GB)

( * ) Notice: Subject to any disclaimer, the term of this patent is extended or adjusted under 35 U.S.C. 154(b) by 0 days.

(21) Appl. No.: 14/741,828

(22) Filed: Jun. 17, 2015

(65) Prior Publication Data
US 2015/0284877 A1    Oct. 8, 2015

Related U.S. Application Data

(63) Continuation-in-part of application No. PCT/GB2013/053320, filed on Dec. 17, 2013.

(30) Foreign Application Priority Data

Dec. 21, 2012  (GB) ...................................... 1223172

(51) Int. Cl.
| | | |
|---|---|---|
| *G01N 33/68* | (2006.01) | |
| *G16B 35/00* | (2019.01) | |
| *G16C 20/60* | (2019.01) | |
| *G01N 33/50* | (2006.01) | |

(52) U.S. Cl.
CPC .......... *G16B 35/00* (2019.02); *G01N 33/505* (2013.01); *G01N 33/6866* (2013.01); *G01N 33/6878* (2013.01); *G16C 20/60* (2019.02); *G01N 2333/57* (2013.01); *G01N 2333/70539* (2013.01); *G01N 2500/04* (2013.01)

(58) Field of Classification Search
None
See application file for complete search history.

(56) References Cited

U.S. PATENT DOCUMENTS

| 5,225,539 A | 7/1993 | Winter | |
| 6,982,086 B2 * | 1/2006 | Haynes | ................ C07K 14/005 424/188.1 |

FOREIGN PATENT DOCUMENTS

| EP | 0 120 694 | 10/1983 |
| EP | 0 125 023 | 11/1984 |
| EP | 0 184 187 | 6/1986 |
| EP | 0 239 400 | 9/1987 |
| GB | 2 188 638 | 10/1987 |
| WO | 93/11161 | 6/1993 |
| WO | 94/13804 | 6/1994 |
| WO | 99/60120 | 11/1999 |
| WO | 03/020763 | 3/2003 |
| WO | 2004/033685 | 4/2004 |
| WO | 2010/133828 | 11/2010 |
| WO | 2011/161127 | 12/2011 |
| WO | 2012/013913 | 2/2012 |

OTHER PUBLICATIONS

Nilges et al (2003 J. Virology 77:5464-74).*
Lee et al (2000 J. Experimental Medicine 200:1455-66).*
Lee et al (J. Experimental Medicine 200:1455-66) (Year: 2004).*
Linnemann et al (Eur. J. Immunol. 31:156-65) (Year: 2001).*
International Search Report and Written Opinion of the International Searching Authority dated Apr. 10, 2014, which issued during prosecution of International Application No. PCT/GB2013/053320.
Altschul, et al. "Gapped BLAST and PSI-BLAST: a new generation of protein database search programs" Nucleic Acids Research 25(17):3389-3402, Jul. 1997.
Amos, et al. "Autoimmunity associated with immunotherapy of cancer" Blood 118(3):499-509, Jul. 2011.
Baeuerle, et al. "BiTE: Teaching antibodies to engage T-cells for cancer therapy" Current Opinion in Molecular Therapeutics 11(1):22-30, 2009.
Bird, et al. "Single-Chain Antigen-Binding Proteins" Science 242:423-426, Oct. 1988.
Cameron, et al. "Immunotherapy Identification of a Titin-Derived HLA-A1-Presented Peptide as a Cross-Reactive Target for Engineered MAGE A3-Directed T Cells" Science Translation Medicine 5:197-200, Aug. 2013.
Chinnasamy, et al. "A TCR Targeting the HLA-A*0201-Restricted Epitope of MAGE-A3 Recognizes Multiple Epitopes of the MAGE-A Antigen Superfamily in Several Types of Cancer" The Journal of Immunology 186 (2):685-696, Jan. 2011.
Dahan, et al. "T-cell-receptor-like antibodies—generation, function and applications" Expert Reviews in Molecular Medicine 14:e6, Feb. 2012.

(Continued)

*Primary Examiner* — Christopher M Gross
(74) *Attorney, Agent, or Firm* — Fenwick & West LLP

(57) ABSTRACT

The invention provides a method for predicting whether a binding peptide, which binds to a target peptide presented by a Major Histocompatibility Complex (MHC) and is for administration to a subject, has the potential to cross react with another peptide in the subject in vivo. The method comprises the steps of identifying at least one binding motif in the target peptide to which the binding peptide binds; and searching for peptides that are present in the subject that comprise the at least one binding motif and that are not the target peptide. The presence of one or more such peptides indicates that the binding peptide has the potential to cross react in vivo.

13 Claims, 8 Drawing Sheets

Specification includes a Sequence Listing.

(56) References Cited

OTHER PUBLICATIONS

Daniel-Meshulam, et al. "How (specific) would you like your T-cells today? Generating T-cell therapeutic function through TCR-gene transfer" Frontiers in Immunology 3(186):1-13, Jul. 2012.
De Castro, et al. "ScanProsite: detection of PROSITE signature matches and ProRule-associated functional and structural residues in proteins" Nucleic Acids Research 34(Web Server Issue):W362-W365, Mar. 2006.
Frankild, et al. "Amino Acid Similarity Accounts for T Cell Cross-Reactivity and for "Holes" in the T Cell Repertoire" PLoS ONE 3(3):e1831, Mar. 2008.
Garboczi, et al. "HLA-A2-peptide complexes: Refolding and crystallization of molecules expressed in Escherichia coli and complexed with single antigenic peptides" Proceedings of the National Academy of Sciences, 89(8):3429-3433, Apr. 1992.
Gebauer, et al. "Engineered protein scaffolds as next-generation antibody therapeutics" Current Opinion in Chemical Biology 13:245-255, 2009.
Hausmann, et al. "Peptide Recognition by Two HLA-A2/Tax(11-19)-Specific T Cell Clones in Relationship to their MHC/Peptide/TCR Crystal Structures" The Journal of Immunology 162:5389-5397, 1997.
Hemmer, et al. "Contribution of Individual Amino Acids within MHC Molecule or Antigenic Peptide to TCR Ligand Potency" The Journal of Immunology 164(2):861-871, Jan. 2000.
Holliger, et al. ""Diabodies": Small bivalent and bispecific antibody fragments" Proceedings of the National Academy of Sciences, 90(14):6444-6448, Jul. 1993.
Holliger, et al. "Engineering bispecific antibodies" Current Opinion in Biotechnology 4(4):446-449, Aug. 1993.
Huston, et al. "Protein engineering of antibody binding sites: Recovery of specific activity in an anti-digoxin single-chain Fv analogue produced in Escherichia coli" Proceedings of the National Academy of Sciences, 85(16):5879-5883, Aug. 1988.
Kosmopoulou, et al. "T-cell epitopes of the La/SSB autoantigen: Prediction based on the homology modeling of HLA-DQ2/DQ7 with the insulin-B peptide/HLA-DQ8 complex" Journal of Computational Chemistry 27(9):1033-1044, Jul. 2006.
Liddy, et al. "Monoclonal TCR-redirected tumor cell killing" Nature Medicine 18(6):980-988, Jun. 2012.
Linnemann, et al. "T-Cell Receptor Gene Therapy: Critical Parameters for Clinical Success" Journal of Investigative Dermatology 131:1806-1816, Jun. 2011.
McCormack, et al. "Bi-specific TCR-anti CD3 redirected T-cell targeting of NY-ESO-1- and LAGE-1-postive tumors" Cancer Immunology Immunotherapy 62(4):773-785, 2013.
Mishra, et al. "Immunoinformatics and modeling perspective of T cell epitope-based cancer immunotherapy: a holistic picture" Journal of Biomolecular Structure & Dynamics 27(3):293-306, Dec. 2009.
Nygren, et al. "Alternative binding proteins: Affibody binding proteins developed from a small three-helix bundle scaffold" FEBS Journal 275(11):2668-2676, 2008.
O'Callaghan, et al. "BirA Enzyme: Production and Application in the Study of Membrane Receptor-Ligand Interactions by Site-Specific Biotinylation" Analytical Biochemistry 266(1):9-15, Jan. 1999.
Restifo, et al. "Adoptive immunotherapy for cancer: harnessing the T cell response" Nature Reviews Immunology 12(4):269-281, Apr. 2012.
Sergeeva, et al. "An anti-PR1/HLA-A2 T-cell receptor-like antibody mediates complement-dependent cytotoxicity against acute myeloid leukemia progenitor cells" Blood 117(16):4262-4272, Apr. 2011.
Skerra, "Alternative binding proteins: Anticalins—harnessing the structural plasticity of the lipocalin ligand pocket to engineer novel binding activities" FEBS Journal 275(11):2677-2683, 2008.
Traunecker, et al. "Bispecific single chain molecules (Janusins) target cytotoxic lymphocytes on HIV infected cells" The EMBO Journal 10(12):3655-3659, 1991.
Udyavar, et al. "Subtle Affinity-Enhancing Mutations in a Myelin Oligodendrocyte Glycoprotein-Specific TCR Alter Specificity and Generate New Self-Reactivity" The Journal of Immunology 182(7):4439-4447, Apr. 2009.
Van Der Loop, et al. "Titin expression as an early indication of heart and skeletal muscle differentiation in vitro. Developmental re-organisation in relation to cytoskeletal constituents" Journal of Muscle Research and Cell Motility 17(1):23-36, 1996.
Ward, et al. "Binding activities of a repertoire of single immunoglobulin variable domains secreted from Escherichia coli" Nature 341(6242):544-546, Oct. 1989.
Watt, "Screening for peptide drugs from the natural repertoire of biodiverse protein folds" Nature Biotechnology 24(2):177-183, Feb. 2006.
Wells, "Systematic Mutational Analyses of Protein-Protein Interfaces" Methods in Enzymology 202:390-411, 1991.
Sidney, J. et al., "Quantitative peptide binding motifs for 19 human and mouse MHC class I molecules derived using positional scanning combinatorial peptide libraries", Immunome Research, 2008, 4:2.
Woolridge, L et al., "A Single Autoimmune T Cell Receptor Recognizes More Than a Million Different Peptides", The Journal of Biological Chemistry, 2012, 287(2):1168-1177.
Rammensee, H. et al., "SYFPEITHI: database for MHC ligands and peptide motifs", Immunogenetics, 1999, 50:213-219.
Jemura, Y. et al., "Systematic Analysis of the Combinatorial Nature of Epitopes Recognized by TCR Leads to Identification of Mimicry Epitopes for Glutamic Acid Decarboxylase 65-Specific TCRs", J Immunol, 2003, 170:947-960.
Macdonald, I.K. et al., "MCH Class I Bound to an Immunodominant Theileria parva Epitope Demonstrates Unconventional Presentation to T Cell Receptors", 2010, PLoS Pathog, 6(10): e1001149.
Petrova, G. et al., "Cross-Reactivity of T Cells and Its Role in the Immune System", 2012, Crit Rev Immunol., 32 (4):349-372.
Brawley and Concannon, "Systematic Mutagenesis of TCR Complementarity-Determining Region 3 Residues: A Single Conservative Substitution Dramatically Improves Response to Both Multiple LHA-DR Alleles and Peptide Variants", 2012, J Immunol, 163: 4946-4952.
Obenaus, M. et al., "Identification of Human T-Cell Receptors With Optimal Affinity to Cancer Antigens Using Antigen-Negative Humanized Mice", Nature Biotechnology, 2015, 33(4):402-409 and Supplementary Material, 1-12.
Bijen, H.M. et al., "Preclinical Strategies to Identify Off-Target Toxicity of High-Affinity TCRs", Molecular Therapy, 2018, 26(5):1206-1214.
Audehm, S. et al., "Key Features Relevant to Select Antigens and TCR From the MHC-Mismatched Repertoire to Treat Cancer", Frontiers in Immunology, 2019, 10:1-16 and Supplementary Material, 1-11.
Maier B. et al., "Multipe Cross-Reactive Self-Ligands for Borrelia Burgdorferi-Specific HLA-DR4-Restricted T Cells", Eur J Immunol, 2000, 30:448-457.
Levitsky, V. et al., "The Clonal Composition of a Peptide-Specific Oligoclonal CTL Repertoire Selected in Response to Persistent EBV Infection is Stable Over Time", J Exp Med, 1998, 161:594-601.
Sethi, D.K. et al., "A Highly Tilted Binding Mode by a Self-Reactive T Cell Receptor Results in Altered Engagement of Peptide and MHC", J Exp Med, 2011, 208(1):91-102.
Grogan, J.L. et al., "Cross-Reactivity of Myelin Basic Protein-Specific T Cells With Multiple Microbial Peptides: Experimental Autoimmune Encephalomyelitis Induction in TCR Transgenic Mice", Journal of Immunology, 1999, 163:3764-3770.
Hard, R.L. et al., "HDAC6 and Ubp-M BUZ Domains Recognize Specific C-Terminal Sequences of Proteins", Biochemistry, 2010, 49(50):10737-10746.
Stone, J.D. and Kranz, D.M., "Role of T Cell Receptor Affinity in the Efficacy and Specificity of Adoptive T Cell Therapies", Front. Immunol., 2013, 4(244):1-16.
Kinnunen, T. et al., "The Immunodominant Epitope of Lipocalin Allergen Bos D 2 is Suboptimal for Human T Cells", Eur J Immunol, 2003, 33:1717-1726.

(56) References Cited

OTHER PUBLICATIONS

Braese, S. "Combinatorial Chemistry on Solid Support: Multiple Peptide Synthesis to Identify Bioactive Hormone Structures", 2007, 2.2.1 Alanine Scan Studies and Single Amino Acid Replacements, p. 253.

Hudson et al., "Multiplex epitope mapping using bacterial surface display reveals both linear and conformational epitopes", Sci Rep, 2012, 2, 706.

Kita et al., "Analysis of TCR Antagonism and Molecular Mimicry of HLA-A*0201-Restricted CTL Epitope in Primary Biliary Cirrhosis", Hepatology, 2002, 36(4 pt 1), pp. 918-926.

Weiss et al., "Rapid Mapping of Protein Functional Epitopes by Combinatorial Alanine Scanning", PNAS, 2000, 97(16), pp. 8950-8954.

Third Party Observation dated Dec. 5, 2017 in related European Patent Application 13811256, publication No. EP2936158.

Glusman et al., "Comparative Genomics of the Human and Mouse T Cell Receptor Loci," Immunity, vol. 15, Issue 3, Sep. 2001, pp. 337-349.

Margulies et al., "Studying interactions involving the T-cell antigen receptor by surface plasmon resonance," Current Opinion in Immunology, vol. 8, Issue 2, Apr. 1996, pp. 262-270.

Matsui et al., "Kinetics of T-cell receptor binding to peptide/I-Ek complexes: correlation of the dissociation rate with T-cell responsiveness," PNAS, Dec. 20, 1994, vol. 91 (26), pp. 12862-12866.

Piepenbrink et al., "Chapter 15—Methods for Quantifying T cell Receptor Binding Affinities and Thermodynamics," Methods in Enzymology, vol. 466, 2009, pp. 359-381.

Preliminary opinion in European patent application No. 13811256.0, dated Jun. 26, 2020, twenty-two pages.

Response on the summons to oral proceedings in opposition proceedings of EP 2936158 (European patent application 13811256.0), Jan. 26, 2021, twenty-two pages.

Third party observations proceedings in proceedings of EP 3373013 (European patent application 18162980.9), Feb. 3, 2021, twenty-five pages.

Wikipedia, In vitro, retrieved online Jan. 2, 2021 from https://en.wikipedia.org/w/index.php?title=In vitro&oldid=991819389, six pages.

\* cited by examiner a3a T cells

IMCmage1

Figure 9

| Antigen | Sequence | | | | | | | | | Normal Tissue Expression | T cell activity (a3a / IMCmage1) |
|---|---|---|---|---|---|---|---|---|---|---|---|
| MAGE-A3 | E | V | D | P | I | G | H | L | Y | Testis | P |
| MAGE-A6 | E | V | D | P | I | G | H | V | Y | Testis | P |
| MAGE-B18 | E | V | D | P | I | R | H | Y | Y | Testis | P low |
| Caveolin-1 | Y | V | D | S | E | G | H | L | Y | Ubiquitous | x |
| FGD5 | E | V | G | P | I | F | H | L | Y | Overexpressed in heart | x |
| ERRFI1 | N | I | D | P | I | T | M | A | Y | Various (overexpressed in aorta) | x |
| RFWD2 | V | V | D | N | I | D | H | L | Y | Various | x |
| DMXL2 | R | V | D | P | I | G | P | L | S | Various | x |
| ATF4 | T | V | N | P | I | G | H | L | P | Under-expressed in heart | x |
| PZP | P | K | A | P | V | G | H | L | Y | Various (overexpressed in heart) | x |
| LMX1A | V | G | N | P | I | D | H | L | Y | Various | x |
| AOX1 | P | E | D | P | I | G | H | P | I | Various | x |
| ARAP3 | L | A | T | L | I | G | H | L | Y | Various (overexpressed in heart) | x |
| MARS2 | A | A | P | H | I | G | H | L | Y | Limited (brain, pancreas) | x |
| SYNGAP1 | E | V | D | P | I | K | C | T | A | Various | x |
| TNRC6B | S | P | D | P | I | G | H | N | P | Various (overexpressed in heart) | x |
| COEA1 | E | V | D | P | I | T | T | F | P | Various | x |
| BRD4 | V | F | D | P | I | G | H | F | T | Various | x |

Figure 10

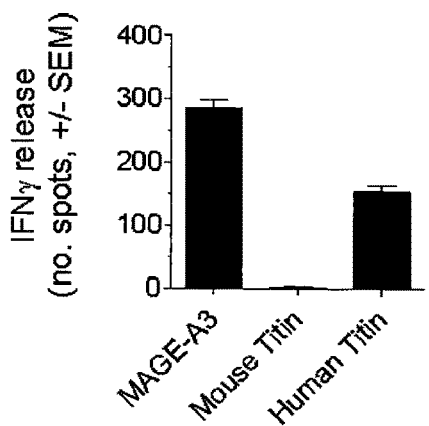

SEQUENCE LISTING

```
<160> NUMBER OF SEQ ID NOS: 48

<210> SEQ ID NO 1
<211> LENGTH: 9
<212> TYPE: PRT
<213> ORGANISM: Homo sapiens

<400> SEQUENCE: 1

Glu Val Asp Pro Ile Gly His Leu Tyr
1               5

<210> SEQ ID NO 2
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 2

Ala Val Asp Pro Ile Gly His Leu Tyr
1               5

<210> SEQ ID NO 3
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 3

Glu Ala Asp Pro Ile Gly His Leu Tyr
1               5

<210> SEQ ID NO 4
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 4
```

```
Glu Val Ala Pro Ile Gly His Leu Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: MAGE A3 peptide alanine mutant

<400> SEQUENCE: 5

Glu Val Asp Ala Ile Gly His Leu Tyr
1               5

<210> SEQ ID NO 6
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 6

Glu Val Asp Pro Ala Gly His Leu Tyr
1               5

<210> SEQ ID NO 7
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 7

Glu Val Asp Pro Ile Ala His Leu Tyr
1               5

<210> SEQ ID NO 8
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 8

Glu Val Asp Pro Ile Gly Ala Leu Tyr
1               5

<210> SEQ ID NO 9
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 9

Glu Val Asp Pro Ile Gly His Ala Tyr
1               5

<210> SEQ ID NO 10
<211> LENGTH: 9
<212> TYPE: PRT
<213> ORGANISM: Artificial sequence
<220> FEATURE:
<223> OTHER INFORMATION: MAGE A3 peptide alanine mutant

<400> SEQUENCE: 10
```

Glu Val Asp Pro Ile Gly His Leu Ala
1               5

<210> SEQ ID NO 11
<211> LENGTH: 9
<212> TYPE: PRT
<213> ORGANISM: Homo sapiens

<400> SEQUENCE: 11

Glu Val Asp Pro Ile Gly His Val Tyr
1               5

<210> SEQ ID NO 12
<211> LENGTH: 9
<212> TYPE: PRT
<213> ORGANISM: Homo sapiens

<400> SEQUENCE: 12

Glu Val Asp Pro Ile Arg His Tyr Tyr
1               5

<210> SEQ ID NO 13
<211> LENGTH: 9
<212> TYPE: PRT
<213> ORGANISM: Homo sapiens

<400> SEQUENCE: 13

Glu Ser Asp Pro Ile Val Ala Gln Tyr
1               5

<210> SEQ ID NO 14
<211> LENGTH: 9
<212> TYPE: PRT
<213> ORGANISM: Homo sapiens

<400> SEQUENCE: 14

Glu Pro Asp Pro Ile Leu Asp Asn Tyr
1               5

<210> SEQ ID NO 15
<211> LENGTH: 9
<212> TYPE: PRT
<213> ORGANISM: Epstein Barr Virus

<400> SEQUENCE: 15

Glu Phe Asp Pro Ile Tyr Pro Ser Tyr
1               5

<210> SEQ ID NO 16
<211> LENGTH: 9
<212> TYPE: PRT
<213> ORGANISM: Clostridium difficile

<400> SEQUENCE: 16

Glu Lys Asp Pro Ile Lys Glu Asn Tyr
1               5

<210> SEQ ID NO 17
<211> LENGTH: 9
<212> TYPE: PRT
<213> ORGANISM: Homo sapiens

<400> SEQUENCE: 17

Tyr Val Asp Ser Glu Gly His Leu Tyr
1               5

```
<210> SEQ ID NO 18
<211> LENGTH: 9
<212> TYPE: PRT
<213> ORGANISM: Homo sapiens

<400> SEQUENCE: 18

Glu Val Gly Pro Ile Phe His Leu Tyr
1               5

<210> SEQ ID NO 19
<211> LENGTH: 9
<212> TYPE: PRT
<213> ORGANISM: Homo sapiens

<400> SEQUENCE: 19

Asn Ile Asp Pro Ile Thr Met Ala Tyr
1               5

<210> SEQ ID NO 20
<211> LENGTH: 9
<212> TYPE: PRT
<213> ORGANISM: Homo sapiens

<400> SEQUENCE: 20

Val Val Asp Asn Ile Asp His Leu Tyr
1               5

<210> SEQ ID NO 21
<211> LENGTH: 9
<212> TYPE: PRT
<213> ORGANISM: Homo sapiens

<400> SEQUENCE: 21

Arg Val Asp Pro Ile Gly Pro Leu Ser
1               5

<210> SEQ ID NO 22
<211> LENGTH: 9
<212> TYPE: PRT
<213> ORGANISM: Homo sapiens

<400> SEQUENCE: 22

Thr Val Asn Pro Ile Gly His Leu Pro
1               5

<210> SEQ ID NO 23
<211> LENGTH: 9
<212> TYPE: PRT
<213> ORGANISM: Homo sapiens

<400> SEQUENCE: 23

Pro Lys Ala Pro Val Gly His Leu Tyr
1               5

<210> SEQ ID NO 24
<211> LENGTH: 9
<212> TYPE: PRT
<213> ORGANISM: Homo sapiens

<400> SEQUENCE: 24

Val Gly Asn Pro Ile Asp His Leu Tyr
1               5
```

<210> SEQ ID NO 25
<211> LENGTH: 9
<212> TYPE: PRT
<213> ORGANISM: Homo sapiens

<400> SEQUENCE: 25

Pro Glu Asp Pro Ile Gly His Pro Ile
1               5

<210> SEQ ID NO 26
<211> LENGTH: 9
<212> TYPE: PRT
<213> ORGANISM: Homo sapiens

<400> SEQUENCE: 26

Leu Ala Thr Leu Ile Gly His Leu Tyr
1               5

<210> SEQ ID NO 27
<211> LENGTH: 9
<212> TYPE: PRT
<213> ORGANISM: Homo sapiens

<400> SEQUENCE: 27

Ala Ala Pro His Ile Gly His Leu Tyr
1               5

<210> SEQ ID NO 28
<211> LENGTH: 9
<212> TYPE: PRT
<213> ORGANISM: Homo sapiens

<400> SEQUENCE: 28

Glu Val Asp Pro Ile Lys Cys Thr Ala
1               5

<210> SEQ ID NO 29
<211> LENGTH: 9
<212> TYPE: PRT
<213> ORGANISM: Homo sapiens

<400> SEQUENCE: 29

Ser Pro Asp Pro Ile Gly His Asn Pro
1               5

<210> SEQ ID NO 30
<211> LENGTH: 9
<212> TYPE: PRT
<213> ORGANISM: Homo sapiens

<400> SEQUENCE: 30

Glu Val Asp Pro Ile Thr Thr Phe Pro
1               5

<210> SEQ ID NO 31
<211> LENGTH: 9
<212> TYPE: PRT
<213> ORGANISM: Homo sapiens

<400> SEQUENCE: 31

Val Phe Asp Pro Ile Gly His Phe Thr
1               5

<210> SEQ ID NO 32
<211> LENGTH: 9

```
<212> TYPE: PRT
<213> ORGANISM: Mus musculus

<400> SEQUENCE: 32

Glu Ser Glu Pro Val Val Ala Gln Tyr
1               5

<210> SEQ ID NO 33
<211> LENGTH: 9
<212> TYPE: PRT
<213> ORGANISM: Homo sapiens

<400> SEQUENCE: 33

Ser Leu Leu Met Trp Ile Thr Gln Cys
1               5

<210> SEQ ID NO 34
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 34

Ala Leu Leu Met Trp Ile Thr Gln Cys
1               5

<210> SEQ ID NO 35
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 35

Ser Ala Leu Met Trp Ile Thr Gln Cys
1               5

<210> SEQ ID NO 36
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 36

Ser Leu Ala Met Trp Ile Thr Gln Cys
1               5

<210> SEQ ID NO 37
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 37

Ser Leu Leu Ala Trp Ile Thr Gln Cys
1               5

<210> SEQ ID NO 38
<211> LENGTH: 9
<212> TYPE: PRT
<213> ORGANISM: Artificial sequence
<220> FEATURE:
<223> OTHER INFORMATION: NY-ESO-1 peptide alanine mutant
```

```
<400> SEQUENCE: 38

Ser Leu Leu Met Ala Ile Thr Gln Cys
1               5

<210> SEQ ID NO 39
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 39

Ser Leu Leu Met Trp Ala Thr Gln Cys
1               5

<210> SEQ ID NO 40
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 40

Ser Leu Leu Met Trp Ile Ala Gln Cys
1               5

<210> SEQ ID NO 41
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 41

Ser Leu Leu Met Trp Ile Thr Ala Cys
1               5

<210> SEQ ID NO 42
<211> LENGTH: 9
<212> TYPE: PRT
<213> ORGANISM: Artificial sequence
<220> FEATURE:
<223> OTHER INFORMATION: NY-ESO-1 peptide alanine mutant

<400> SEQUENCE: 42

Ser Leu Leu Met Trp Ile Thr Gln Ala
1               5

<210> SEQ ID NO 43
<211> LENGTH: 9
<212> TYPE: PRT
<213> ORGANISM: Homo sapiens

<400> SEQUENCE: 43

His Leu Cys Met Trp Ser Asp Gly Cys
1               5

<210> SEQ ID NO 44
<211> LENGTH: 9
<212> TYPE: PRT
<213> ORGANISM: Homo sapiens

<400> SEQUENCE: 44

Gly Leu Leu Asn Trp Ile Thr Gly Ala
1               5
```

```
<210> SEQ ID NO 45
<211> LENGTH: 9
<212> TYPE: PRT
<213> ORGANISM: Mus musculus

<400> SEQUENCE: 45

His Leu Cys Met Trp Asn Asp Gly Cys
1               5

<210> SEQ ID NO 46
<211> LENGTH: 9
<212> TYPE: PRT
<213> ORGANISM: Mus musculus

<400> SEQUENCE: 46

Gly Leu Leu Asn Cys Leu Thr Gly Ala
1               5

<210> SEQ ID NO 47
<211> LENGTH: 9
<212> TYPE: PRT
<213> ORGANISM: Artificial sequence
<220> FEATURE:
<223> OTHER INFORMATION: peptide binding motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 47

Glu Xaa Asp Pro Ile Xaa Xaa Xaa Tyr
1               5

<210> SEQ ID NO 48
<211> LENGTH: 9
<212> TYPE: PRT
<213> ORGANISM: Artificial sequence
<220> FEATURE:
<223> OTHER INFORMATION: peptide binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 48

Xaa Leu Xaa Met Trp Ile Thr Gln Xaa
1               5
```

METHOD FOR PREDICTING THE OFF-TARGET BIDING OF A PEPTIDE WHICH BINDS TO A TARGET PEPTIDE PRESENTED BY A MAJOR HISTOCOMPATIBILITY COMPLEX

RELATED APPLICATIONS AND INCORPORATION BY REFERENCE

This application is a continuation-in-part application of international patent application Serial No. PCT/GB2013/053320 filed 17 Dec. 2013, which published as PCT Publication No. WO 2014/096803 on 26 Jun. 2014, which claims benefit of GB patent application Serial No. 1223172.6 filed 21 Dec. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jun. 16, 2015, is named 44172002021 SL.txt and is 9,059 bytes in size.

FIELD OF THE INVENTION

The present invention relates to a method for predicting whether a binding peptide, which binds to a target peptide, preferably a target peptide that is presented in the context of major histocompatibility complex (MHC), and is for administration to a subject, will cross react with another peptide in the subject in vivo.

BACKGROUND OF THE INVENTION

MHC class I and class II are immunoglobulin superfamily proteins specialised for antigen presentation, with a polymorphic peptide binding site which enables them to present a diverse array of short peptide fragments at the surface of the antigen presenting cell. Peptides presented by MHC are derived from proteins which have been proteosomally processed within the cell. In humans, MHC molecules are known as human leukocyte antigens (HLA).

A number of emerging immunotherapies rely on the administration to a subject to be treated of a binding peptide that binds a target peptide-MHC complex. The binding peptide may be an immune binding peptide such as, for example, an antibody or antigen binding fragment thereof or a T cell receptor or antigen binding fragment thereof. Such binding peptides bind to a binding sequence, comprising the amino acid sequence of the target MHC presented peptide. Often the binding sequence of the target peptide is known.

There is a risk with such therapies that the binding peptide binds to peptides other than the target peptide (referred to herein as "off target peptides"), causing unwanted side effects. It is therefore desirable to identify whether such off target peptides exist. This allows binding peptides to be chosen and designed that do not bind to off target peptides and consequently have a far greater chance of not causing unwanted side effects.

Reasons for unwanted side effects derived from off target specificities in adoptive T cell therapy are; mispairing of transduced TCR chains with endogenous chains, insertion mutagenesis associated with TCR transduction, or alloreactivity (Amos et al., Blood 2011, 118(3):499-509; Daniel-Meshulam et al., Front Immunol 2012, 3:186). To date, the way to prevent off target toxicity is to include apoptosis genes to destroy T cells if toxicity arises after administration to the patient (Restifo, et al., Nat Rev Immunol 2012, 12(4): 269-81.)

Thus a person skilled in the art would be motivated to provide mechanisms that deal with binding to off target peptides after administration of a binding peptide. It is therefore unlikely that a person skilled in the art would consider trying to identify off target peptides before the binding peptide is administered. In the highly unlikely event that the skilled person took this latter approach, one option would be to search protein sequence databases for peptides with similarity to the target MHC presented peptide. But, this often returns a large number of peptides, all of which would need to be tested and even then off-target peptides may not be identified. Lowering the stringency of the search parameters would further increase the number of potential epitopes that would have to be tested and again may still not reveal off target peptides. Alternatively, the skilled person may measure any immune response generated by the binding peptide in the presence of cells derived from normal tissue(s) (which preferably do not express the target peptide). However, this can be a difficult process, depending on the number and type of cells tested. Furthermore, primary cells cultured in vitro, may have a different protein expression profile compared to the same cell type in vivo. This may result in a false assessment of potential cross reactivity in vivo. Finally, the skilled person may use animal models to measure any immune response generated by the binding peptide. Because of the differences between human protein sequences and those of the animal, the absence of unwanted side effects in the animal may not translate to humans.

Thus, these approaches do not accurately indicate, especially when administered to a subject, whether the binding peptide will indeed give rise to unwanted side effects derived from off target specificities, especially in an individualised or personalised setting. In short, any attempt heretofore to identify off target peptides before the binding peptide is administered had no reasonable expectation of success. Indeed, as is explained in more detail below, the inventors have found that such approaches will not necessarily identify off target peptides that cause an unwanted side effect. Although these approaches were performed on the a3a T cells described in the examples below, off-target activation of a3a T cells only become apparent when the binding peptide was administered to patients (manuscript in preparation).

Citation or identification of any document in this application is not an admission that such document is available as prior art to the present invention.

SUMMARY OF THE INVENTION

It is therefore desirable to provide an alternative method for predicting whether a binding peptide will or at least is likely to bind to an off target peptide, which addresses drawbacks of the prior art.

In an aspect, the present invention provides a method for predicting whether a binding peptide, which binds to a target peptide presented by a Major Histocompatibility Complex (MHC) and is for administration to a subject, has the potential to cross react with another peptide in the subject in vivo, the method which may comprise:

identifying at least one binding motif in the target peptide to which the binding peptide binds; and searching for peptides that are present in the subject that may comprise the at least one binding motif and that are not the target peptide, wherein the presence of one or more such peptides indicates that the binding peptide has the potential to cross react in vivo.

In another aspect, the invention comprehends a method of treating a human or animal mammalian subject in need thereof—advantageously which may comprise providing individualized or personalized treatment involving a binding peptide—which may comprise:

predicting whether the binding peptide, which binds to a target peptide presented by a Major Histocompatibility Complex (MHC) in the subject to thereby provide said treatment and is for administration to the subject, has the potential to cross react with another peptide in the subject in vivo, which may comprise:

identifying at least one binding motif in the target peptide to which the binding peptide binds; and searching for peptides that are present in the subject that may comprise the at least one binding motif and that are not the target peptide, wherein the presence of one or more such peptides indicates that the binding peptide has the potential to cross react in vivo, and the absence of one or more of such peptides indicates that the binding peptide has the potential not to react in vivo.

The at least one binding motif may be identified by:

creating a series of mutants of the target peptide, each mutant having the amino acid residue at one position in the binding sequence thereof that is involved in binding to the binding peptide substituted for an alternative amino acid, such that over the series of mutants the amino acid residue in each position in the binding sequence is substituted for an alternative amino acid; and testing each mutant in the series for its activity relative to the wild type target peptide, wherein an amino acid residue at a position within the binding sequence is identified as being part of the binding motif if the mutant in which the amino acid at that position is mutated to an alternative amino acid has a substantial loss of activity relative to the wild type target peptide.

Methods of the invention may further comprise, where an amino acid residue at a position in the binding sequence is not identified as being part of the binding motif, substituting this position with at least one additional amino acid and testing for activity relative to the wild type peptide, wherein amino acid substitutions which result in a substantial loss of activity relative to the wild type target peptide are considered to be non-tolerated amino acids and not part of the binding motif and/or amino acid substitutions which do not result in a substantial loss of activity relative to the wild type target peptide are considered as part of the binding motif.

Methods of the invention may further comprise creating a series of mutants, each mutant having the amino acid residue at one position in the binding sequence substituted for an alternative amino acid, such that over the series of mutants the amino acid residue in each position in the binding sequence is substituted for all alternative amino acids, and testing each mutant in the series for activity relative to the wild type peptide, wherein amino acid substitutions which result in a substantial loss of activity relative to the wild type target peptide are considered to be non-tolerated amino acids and not part of the binding motif and/or amino acids substitutions which do not result in a substantial loss of activity relative to the wild type target peptide are considered as part of the binding motif.

The activity that is tested may be the ability of the mutant to bind to the binding peptide and/or to elicit the biological response caused by binding to the binding peptide.

The alternative amino acid may have a different side chain to that of the amino acid for which it is being substituted.

The alternative amino acid may be one that does not appear in the sequence that is involved in binding to the target peptide.

The alternative amino acid may be alanine or glycine.

The search may be carried out for peptides that are expressed in selected tissue(s) and/or accessible to the binding peptide.

Methods of the invention may further comprise testing binding to the target peptide of any peptide that is present in the subject that may comprise the at least one binding motif.

Methods of the invention may further comprise:

when there is the absence of one or more of such peptides and hence the indication that the binding peptide has the potential not to cross react in vivo, administering a treatment effective amount of the binding peptide to the subject, and/or when there is the presence of one or more such peptides and hence an indication that the binding peptide has the potential to cross react in vivo, identifying the potential for each peptide to cause off target side effects in vivo, and where necessary, preparing an alternative binding peptide having the absence of one or more of such peptides and hence the indication that the alternative binding peptide has the potential not to cross react in vivo, and administering a treatment effective amount of the alternative binding peptide to the subject.

The treatment effective amount of the binding peptide is that amount typically given to the suitable mammalian patient. Thus, the invention comprehends testing known binding peptide treatments for whether such treatment binding peptides will bind to peptides other than the target peptide. The treatment effective amount of the alternative binding peptide is within the ambit of the skilled person from this disclosure and the knowledge in the art. For example, the treatment effective amount can be determined by comparing the binding properties and/or ability to elicit the desired treatment biological response of the binding peptide with the binding properties and/or ability to elicit the desired treatment biological response of the alternative binding peptide, and adjusting the dosage of the binding peptide based on the difference in binding and/or ability to elicit the biological response of the alternative binding peptide in comparison with the binding and/or ability to elicit the biological response of the binding peptide. In advantageous embodiments, the alternative binding peptide has binding properties and/or biological response eliciting properties akin to that of the binding peptide, and hence its dosage or amount to be administered is analogous to that of the binding peptide.

In certain aspects, the invention therefore provides an improvement in a method of treating a human or animal mammalian subject in need thereof which may comprise administering a binding peptide. This improvement may comprise:
predicting whether the binding peptide, which binds to a target peptide presented by a Major Histocompatibility Complex (MHC) in the subject to thereby provide said treatment and is for administration to the subject, has the potential to cross react with another peptide in the subject in vivo, which may comprise:
identifying at least one binding motif in the target peptide to which the binding peptide binds; and
searching for peptides that are present in the subject that may comprise the at least one binding motif and that are not the target peptide,
wherein the presence of one or more such peptides indicates that the binding peptide has the potential to cross react in vivo, and the absence of one or more of such peptides indicates that the binding peptide has the potential to not to react in vivo; and,
when there is the absence of one or more of such peptides and hence the indication that the binding peptide has the potential will not to react in vivo, and/or when binding to the off target peptide is not expected to cause unwanted side effects in vivo, administering a treatment effective amount of the binding peptide to the subject.

This method can include, when there is the presence of one or more such peptides and hence an indication that the binding peptide has the potential to cross react in vivo, preparing an alternative binding peptide having the absence of one or more of such peptides and hence the indication that the alternative binding peptide has the potential not to cross react in vivo, and administering a treatment effective amount of the alternative binding peptide to the subject.

Moreover, the invention has utility in the preparation of pharmaceutical compositions which may comprise a binding peptide. In this respect, the invention provides a method for preparing a pharmaceutical composition which may comprise a binding peptide, or an improvement to methods for preparing a pharmaceutical composition which may comprise a binding peptide, which may comprise:
predicting whether the binding peptide, which binds to a target peptide presented by a Major Histocompatibility Complex (MHC) in the subject to thereby provide said treatment and is for administration to the subject, has the potential to cross react with another peptide in the subject in vivo, which may comprise:
identifying at least one binding motif in the target peptide to which the binding peptide binds; and
searching for peptides that are present in the subject that may comprise the at least one binding motif and that are not the target peptide,
wherein the presence of one or more such peptides indicates that the binding peptide has the potential to cross react in vivo, and the absence of one or more of such peptides indicates that the binding peptide has the potential not to react in vivo.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention solely to the specific embodiments described, may best be understood in conjunction with the accompanying drawings, wherein:

FIG. 9 shows details of 15 peptides identified in a BLAST search carried out to find human peptides with a similar sequence to MAGE A3 peptide. Activation of a3a T cells or IMCmage1 redirected T cells, as determined by IFNγ ELISpot, is indicated.

FIG. 10 shows activation of a3a T cells, as determined by IFNγ ELISpot, in response to peptide-pulsed cells presenting either MAGE A3, human Titin, or mouse Titin.

DETAILED DESCRIPTION

Figure 1:
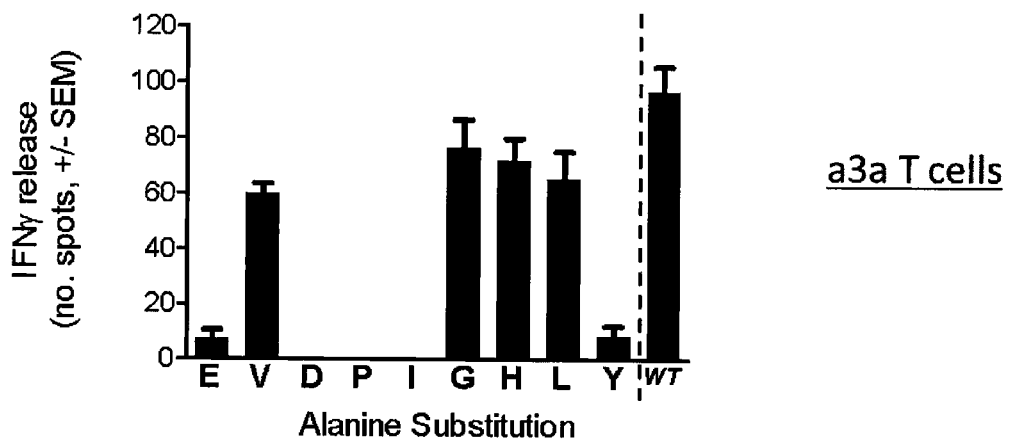
FIG. 1 shows IFNγ production by a3a T cells in response to peptide-pulsed cells presenting either MAGE A3 peptide (denoted WT), or alanine-substituted peptides.

The inventors have found that, by identifying the binding motif in the target peptide to which the binding peptide binds, rather than the known binding sequence, off target peptides—that have the potential to, or will, cross react in vivo—can be identified far more accurately. If off target peptides are found, this allows binding peptides to be altered so that they do not bind to these off target peptides.

The binding motif(s) may be identified by creating a series of mutants of the target peptide, each mutant having the amino acid residue at one position in the sequence thereof that is involved in binding to the binding peptide (the "binding sequence") substituted for an alternative amino acid, such that over the series of mutants the amino acid residue in each position in the binding sequence is substituted for an alternative amino acid. Each mutant in the series is then tested for its activity relative to the wild type target peptide. An amino acid residue at a position within the binding sequence may be identified as being part of the binding motif if the mutant in which the amino acid at that position is mutated to an alternative amino acid has a substantial loss of activity relative to the wild type target peptide, such as 50, 55, 60, 65, 70, 75, 80, 85, 90% or greater loss of activity. This may result in a binding motif which may comprise amino acid(s) at one or a plurality of positions (such as 2, 3, 4, 5, 6, 7, 8, 9, 10 or more) within the binding sequence being identified.

Where an amino acid residue at a position in the binding sequence is not identified as being part of the binding motif (using the technique described above for example), this position may be further substituted with at least one additional amino acid and tested for activity relative to the wild type peptide. Amino acid substitutions which result in a substantial loss of activity relative to the wild type target peptide, such as 50, 55, 60, 65, 70, 75, 80, 85, 90% or greater loss of activity, are considered to be non-tolerated amino acids and/or not part of the binding motif. Conversely, amino acid substitutions which do not result in a substantial loss of activity (for example of at least 50%) relative to the wild type target peptide may be considered as part of the binding motif. This may result in a binding motif as defined above and additionally in which one or a plurality of positions are represented by more than one but not all amino acids.

Alternatively or additionally, a series of mutants may be made in which the amino acid residue at each position of the binding sequence is mutated to all alternative amino acids (relative to the wild type amino acid). For a binding sequence of nine amino acids, this would mean 171 peptides. Each mutant in the series is tested for activity relative to the wild type peptide. Amino acid substitutions which result in a substantial loss of activity relative to the wild type target peptide, such as 50, 55, 60, 65, 70, 75, 80, 85, 90% or greater loss of activity, are considered to be non-tolerated amino acids and/or not part of the binding motif. Conversely, amino acid substitutions which do not result in a substantial loss of activity (for example of at least 50%) relative to the wild type target peptide may be considered as part of the binding motif. This may result in a binding motif in which each position is represented by at least one but not all amino acids.

The activity that is tested may be the ability of the mutant to bind to the binding peptide (this can be measured using Surface Plasmon Resonance for example) and/or to elicit the biological response caused by binding to the binding peptide. The biological response may be, for example, activation of immune system cells such as T cells, measured by cytokine production or destruction of the target cell; activation of an enzyme, measured by accumulation of product or disappearance of substrate; or activation of a signalling cascade (measured by monitoring protein phosphorylation, or changes in gene expression and protein production).

The alternative amino acid substituted into the mutants may be alanine, glycine or indeed any amino acid, provided that it has a different side chain to that of the amino acid for which it is being substituted. Preferably, the alternative amino acid is one that does not appear in the binding sequence. Thus, any one of the following amino acids may be used: alanine, asparagine, aspartic acid, arginine, cysteine, glutamine, glycine, glutamic acid, histidine, isoleucine, lysine, leucine, phenylalanine, methionine, serine, proline, tryptophan, threonine, tyrosine, valine, as well as non-naturally occurring amino acids. Such techniques, known as "amino acid scanning", are known in the art and have been used to determine a binding motif. See Wells, *Methods Enzymol* 1991; 202: 390-411 for example. A similar approach is also known for detecting other specificities of a T cell receptor (for example Udyavar et al. *J Immunol* 2009; 182(7):4439-47). However, such amino acid scanning has not been used to identify off-target peptides which may cause undesirable side effects.

Once the binding motif has been identified, protein databases may be searched for proteins which contain the binding motif. Suitable protein databases include but are not limited to UniProtKB/Swiss-Prot (http://www.uniprot.org/), Protein Information Resource (PIR) (http://pir.georgetown.edu/pirwww/index.shtml), and/or Reference Sequence (RefSeq) (www.ncbi.nlm.nih.gov/RefSeq).

Searching for a peptide motif may be carried out using any one of a number of tools, which may be found on bioinformatics resource sites such as ExPASY (http://www.expasy.org/). For example, the search tool ScanProsite identifies user-defined motifs in all protein sequences in the UniProtKB/Swiss-Prot Protein Knowledgebase (De Castro et al. *Nucleic Acids Res.* 2006 Jul. 1; 34 (Web Server issue):W362-5).

It is preferred that peptides containing the exact binding motif, i.e. with 100% identity to the binding motif, are identified. However, proteins containing motifs that have less than 100% identity to the binding motif may be identified. For the purposes of searching, the binding motif may be modified to include ambiguity at certain positions, for example with amino acids which have similar properties (e.g. leucine/isoleucine, etc), or where it is already known in the literature that a particular amino acid is tolerated at a certain position (such as HLA anchor residues).

The search may be carried out for peptides that are of human origin or of organisms which are commonly present in humans, such as viral or bacterial pathogens, or commensal bacteria. However, where the method of the present invention is applied to non-human animals, such as non-human mammals, the search may be carried out for peptides that are of the relevant non-human animal origin or of organisms which are commonly present in such non-human animals. Additionally or alternatively, the search may be carried out for peptides that are expressed in selected tissue(s) and/or accessible to the binding peptide. Such information may be obtained from the literature.

Peptides identified in the search as which may comprise the at least one binding motif may be confirmed as an off target peptide and cross reacting with binding peptide by determining the ability of the identified peptide to bind to the binding peptide (for example using Surface Plasmon Resonance), or assessing the biological response generated by binding of the binding peptide to the identified peptide. The biological response may be for example, activation of immune system cells such as T cells, measured by cytokine production or destruction of the target cell; activation of an enzyme, measured by accumulation of product or disappearance of substrate; or, activation of a signalling cascade (measured by monitoring protein phosphorylation, or changes in gene expression and protein production).

Once one or more off target peptides have been identified, the potential of the (or each) off target peptide to cause unwanted side effects when bound by the binding peptide may be determined. This may include searching literature sources to determine expression of the off target peptide in normal tissue. For example, where expression of the off target peptide in normal tissue is non-existent or limited (for example with cancer testis antigens), the binding peptide may be considered suitable for administration in vivo. In cases where expression of the off target peptide in normal tissue is widespread or is in critical tissues, such as heart cells, binding may optionally be additionally confirmed in vitro using cells which express the off target peptide. In some situations the binding peptide may not be administered in vivo because of the cross reaction that this can cause. The binding peptide may be redesigned so that there is no longer any cross reactivity to the off target peptide(s), while maintaining binding, preferably with high affinity, to the target peptide. For example, T cell receptors can be redesigned by mutagenesis using the methods described in WO 03/020763. Where redesigning does not prevent cross reactivity to the off target peptide, an alternative binding peptide may be sought, for example, an alternative T cell receptor, which binds the target peptide.

If no off target peptides are found, or if the binding to the off target peptides is not expected to cause unwanted side effects (for example by virtue of the off target peptide being expressed in limited or non-critical tissues), the binding peptide may be used in a method of preventing or treating a disease or condition which is ameliorated by administration of the binding peptide. Methods of treatment include but are not limited to immunotherapies; for example, administration to a patient of modified T cells (adoptive therapy), such as those transduced with affinity enhanced T cell receptors or chimeric antibody receptors; administration of monoclonal antibodies or monoclonal antibody fragments, especially TCR-like antibodies; administration of novel bi-specific immunotherapeutic agents such as ImmTACs (Immune mobilising TCRs against cancer) (Liddy, et al. (2012) *Nat Med* 18: 980-987) or BiTEs (Bispecific T cell engaging antibodies) (Baeuerle, et al. (2009). *Curr Opin Mol Ther* 11(1): 22-30).

Such treatments may be provided in a pharmaceutical composition together with one or more pharmaceutically acceptable carriers or excipients. Therapeutic TCRs, or cells, will usually be supplied as part of a sterile, pharmaceutical composition which will normally include a pharmaceutically acceptable carrier. This pharmaceutical composition may be in any suitable form (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as a parenteral (including subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc.; for example, a suitable dose range for an ImmTAC reagent may be between 25 ng/kg and 50 µg/kg. A physician will ultimately determine appropriate dosages to be used.

In the present invention, the binding peptide that binds to MHC presented peptide may be an immune binding peptide, which may be an immunotherapeutic peptide. Binding peptides can be derived from natural sources, or they may be partly or wholly synthetically produced. Examples of immune binding peptides include T cell receptors ("TCRs"—which term includes antigen binding fragments of T cell receptors). As is described in WO 99/60120, TCRs mediate the recognition of specific Major Histocompatibility Complex (MHC)-peptide complexes by T cells and, as such, are essential to the functioning of the cellular arm of the immune system. The TCR is a heterodimeric cell surface protein of the immunoglobulin superfamily which is associated with invariant proteins of the CD3 complex involved in mediating signal transduction. TCRs exist in $\alpha\beta$ and $\gamma\delta$ forms, which are structurally similar but T cells expressing them have quite distinct anatomical locations and probably functions. The extracellular portion of the receptor consists of two membrane-proximal constant domains, and two membrane-distal variable domains bearing polymorphic loops analogous to the complementarity determining regions (CDRs) of antibodies. It is these loops which form the binding site of the TCR molecule and determine peptide specificity.

The TCR may be in soluble form (e.g. having no transmembrane or cytoplasmic domains), for example a monoclonal TCR as described in WO03/020763, and/or in single chain form, as described in WO2004/033685. For stability, soluble TCRs preferably have an introduced disulphide bond between residues of the respective constant domains, as described, for example, in WO 03/020763. Single chain formats include $\alpha\beta$ TCR polypeptides of the V$\alpha$-L-V$\beta$, V$\beta$-L-V$\alpha$, V$\alpha$-C$\alpha$-L-V$\beta$ or V$\alpha$-L-V$\beta$-C$\beta$ types, wherein V$\alpha$ and V$\beta$ are TCR $\alpha$ and $\beta$ variable regions respectively, C$\alpha$ and C$\beta$ are TCR $\alpha$ and $\beta$ constant regions respectively, and L is a linker sequence. Alternatively or additionally, the TCR may be fused to an immune effector domain for use as a targeting agent for delivering therapeutic agents to an antigen presenting cell. Such therapeutic agents include for example antibodies or antibody fragments such as an anti-CD3 fragment, immunomodulators such as cytokines, enzymes such as perforin, or chemotherapeutic agents, such as cis-platin. TCRs may also be expressed on a cell, such as a T cell. Said T cells may be used in adoptive therapy.

Other binding peptides encompassed by the present invention include antibodies, such as TCR like antibodies, which have been engineered to bind to MHC presented peptides (for example see, Sergeeva, A., G. et al. (2011). Blood 117(16): 4262-72 and/or Dahan, R., and Y. Reiter. 2012. Expert Rev Mol Med. 14:e6. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. Examples of antibodies are the immunoglobulin isotypes (e.g., IgG, IgE, IgM, IgD and IgA) and their isotypic subclasses; fragments which may comprise an antigen binding domain such as Fab, scFv, Fv, dAb, Fd; and diabodies. Antibodies may be polyclonal or monoclonal. A monoclonal antibody may be referred to herein as "mab".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering antibody fragments, derivatives, functional equivalents and homologues of antibodies, humanised antibodies, including any polypeptide which may comprise an immunoglobulin binding domain, whether natural or wholly or partially synthetic. Chimeric molecules which may comprise an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment which may comprise two linked Fab fragments; (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)). Diabodies are multimers of polypeptides, each polypeptide which may comprise a first domain which may comprise a binding region of an immunoglobulin light chain and a second domain which may comprise a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991). Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. An "antigen binding domain" is the part of an antibody which may comprise the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

Also encompassed within the present invention are binding peptides that bind to MHC presented peptides and are based on engineered protein scaffolds. Protein scaffolds are derived from stable, soluble, natural protein structures which have been modified to provide a binding site for a target molecule of interest. Examples of engineered protein scaffolds include, but are not limited to, affibodies, which are based on the Z-domain of staphylococcal protein A that provides a binding interface on two of its α-helices (Nygren, P. A. (2008). FEBS J 275(11): 2668-76); anticalins, derived from lipocalins, that incorporate binding sites for small ligands at the open end of a beta-barrel fold (Skerra, A. (2008) FEBS J 275(11): 2677-83), nanobodies, and DARPins. Engineered protein scaffolds are typically targeted to bind the same antigenic proteins as antibodies, and are potential therapeutic agents. They may act as inhibitors or antagonists, or as delivery vehicles to target molecules, such as toxins, to a specific tissue in vivo (Gebauer, M. and A. Skerra (2009). Curr Opin Chem Biol 13(3): 245-55). Short peptides may also be used to bind a target protein.

Phylomers are natural structured peptides derived from bacterial genomes. Such peptides represent a diverse array of protein structural folds and can be used to inhibit/disrupt protein-protein interactions in vivo (Watt, P. M. (2006). Nat Biotechnol 24(2): 177-83)].

Although the present invention has been described with reference to predicting whether a binding peptide, which binds to a target peptide that is presented in the context of MHC, will cross react with another peptide in a subject in vivo, it is to be understood that the techniques described herein can be applied to any target peptide, regardless of whether it is presented in the context of MHC. Thus, binding peptide and target peptide may be any pair of molecules which have binding specificity for one another. Other examples of such pairs of molecules include hormone-hormone receptor, receptor-ligand, enzyme-substrate. With regard to the methods of the invention, as an example, the invention can be practiced with regard to any known antibody treatments. Examples of FDA-approved therapeutic monoclonal antibodies are set forth in the following table.

Example FDA approved therapeutic monoclonal antibodies

| Antibody | Brand name | Company | Approval date | Type | Target | Indication (Targeted disease) |
|---|---|---|---|---|---|---|
| Abciximab | ReoPro | Eli Lilly | 1994 | chimeric | inhibition of glycoprotein IIb/IIIa | Cardiovascular disease |
| Adalimumab | Humira | Abbot | 2002 | human | inhibition of TNF-α signaling | Several auto-immune disorders |
| Alemtuzumab | Campath | Genzyme | 2001 | humanized | CD52 | Chronic lymphocytic leukemia |
| Basiliximab | Simulect | Novartis | 1998 | chimeric | IL-2Rα receptor (CD25) | Transplant rejection |
| Belimumab | Benlysta | Glaxo SmithKline | 2011 | human | inihibition of B-cell activating factor | Systemic lupus erythematosus[disambiguation needed] |
| Bevacizumab | Avastin | Genentech/Roche | 2004 | humanized | Vascular endothelial growth factor (VEGF) | Colorectal cancer, Age related macular degeneration (off-label) |
| Brentuximab vedotin | Adcetris | | 2011 | Chimeric | CD30 | Anaplastic large cell lymphoma (ALCL) and Hodgkin lymphoma |
| Canakinumab | Ilaris | Novartis | 2009 | Human | IL-1β | Cryopyrin-associated periodic syndrome (CAPS) |
| Cetuximab | Erbitux | Bristol-Myers Squibb/Eli Lilly/Merck KGaA | 2004 | chimeric | epidermal growth factor receptor | Colorectal cancer, Head and neck cancer |
| Certolizumab pegol[19] | Cimzia | UCB (company) | 2008 | humanized | inhibition of TNF-α signaling | Crohn's disease |
| Daclizumab | Zenapax | Genentech/Roche | 1997 | humanized | IL-2Rα receptor (CD25) | Transplant rejection |
| Denosumab | Prolia, Xgeva | Amgen | 2010 | Human | RANK Ligand inhibitor | Postmenopausal osteoporosis, Solid tumor's bony metastases |
| Eculizumab | Soliris | Alexion Pharmaceuticals | 2007 | humanized | Complement system protein C5 | Paroxysmal nocturnal hemoglobinuria |
| Efalizumab | Raptiva | Genentech/Merck Serono | 2002 | humanized | CD11a | Psoriasis |
| Gemtuzumab | Mylotarg | Wyeth | 2000 | humanized | CD33 | Acute myelogenous leukemia (with calicheamicin) |
| Golimumab | Simponi | Johnson & Johnson/Merck & Co, Inc. | 2009 | Human | TNF-alpha inihibitor | Rheumatoid arthritis, Psoriatic arthritis, and Ankylosing spondylitis |
| Ibritumomab tiuxetan | Zevalin | Spectrum Pharmaceuticals, Inc. | 2002 | murine | CD20 | Non-Hodgkin lymphoma (with yttrium-90 or indium-111) |
| Infliximab | Remicade | Janssen Biotech, Inc./Merck & Co | 1998 | chimeric | inhibition of TNF-α signaling | Several autoimmune disorders |
| Ipilimumab (MDX-101) | Yervoy | | 2011 | Human | blocks CTLA-4 | Melanoma |
| Muromonab-CD3 | Orthoclone OKT3 | Janssen-Cilag | 1986 | murine | T cell CD3 Receptor | Transplant rejection |
| Natalizumab | Tysabri | Biogen Idec/Élan | 2006 | humanized | alpha-4 (α4) integrin, | Multiple sclerosis and Crohn's disease |
| Ofatumumab | Arzerra | | 2009 | Human | CD20 | Chronic lymphocytic leukemia |
| Omalizumab | Xolair | Genentech/Novartis | 2004 | humanized | immunoglobulin E (IgE) | mainly allergy-related asthma |
| Palivizumab | Synagis | MedImmune | 1998 | humanized | an epitope of the RSV F protein | Respiratory Syncytial Virus |
| Panitumumab | Vectibix | Amgen | 2006 | human | epidermal growth factor receptor | Colorectal cancer |
| Ranibizumab | Lucentis | Genentech/Novartis | 2006 | humanized | Vascular endothelial growth factor A (VEGF-A) | Macular degeneration |
| Rituximab | Rituxan, Mabthera | Biogen Idec/Genentech | 1997 | chimeric | CD20 | Non-Hodgkin lymphoma |

| Antibody | Brand name | Company | Approval date | Type | Target | Indication (Targeted disease) |
|---|---|---|---|---|---|---|
| Tocilizumab (or Atlizumab) | Actemra and RoActemra | | 2010 | Humanised | Anti- IL-6R | Rheumatoid arthritis |
| Tositumomab | Bexxar | GlaxoSmithKline | 2003 | murine | CD20 | Non-Hodgkin lymphoma |
| Trastuzumab | Herceptin | Genentech | 1998 | humanized | ErbB2 | Breast cancer |

Example FDA approved therapeutic monoclonal antibodies

In this regard, mention is also made of bispecific antibodies with which the invention can also be practiced. Bispecific antibodies are a particular class of therapeutic antibodies that have yielded promising results in clinical trials, and in April 2009, the bispecific antibody catumaxomab was approved in the European Union.

The methods of the invention can be practiced with such binding peptides as these monoclonal and bispecific antibody treatments, and hence the skilled person readily knows the formulation and dose and means to administer if there is no cross reactivity detected using the instant invention, and from the dosages of these known binding peptides, can readily determine, using the herein disclosure and the knowledge in the art, the formulation, and dose and means to administer alternative binding peptides.

Preferred features of each aspect of the invention are as for each of the other aspects mutatis mutandis. The prior art documents mentioned herein are incorporated to the fullest extent permitted by law. The present invention will be further illustrated in the following Examples which are given for illustration purposes only and are not intended to limit the invention in any way; but rather, the Applicants reserve the right to both generalise from the Examples when claiming, and provide from the Examples specific claims.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The present invention will now be described with reference to the following non-limiting examples.

Example 1

The target MHC presented peptide used in this example is derived from human cancer testis antigen MAGE A3 and has the following amino acid sequence; EVDPIGHLY. MAGE A3 peptide is presented on antigen presenting cells in the context of HLA-A*01.

The binding peptide used in this example may comprise a modified T cell receptor (TCR) which has been engineered to possess enhanced affinity for MAGE A3 peptide. Methods to produce affinity enhanced TCRs are known in the art (for example, phage display WO 03/020763). The native MAGE A3 TCR was obtained from a MAGE A3 T cell clone, as described in WO2012/013913. Two versions of the modified MAGE A3 TCR are used. A moderately affinity enhanced version, expressed by transduced T cells (termed a3a T cells) as described in WO2012/013913, and a high affinity version, produced as a soluble protein fused to a T cell activating anti-CD3 fragment (termed IMCmage1), according to the method of WO2010/133828.

1.1 Identification of the Binding Motif

Variants of the native MAGE A3 peptide were obtained in which each amino acid position was sequentially replaced with alanine, as shown below (in each case the alanine substitution is underlined). Peptides were obtained from Peptide Protein Research Limited, UK.

```
AVDPIGHLY

EADPIGHLY

EVAPIGHLY

EVDAIGHLY

EVDPAGHLY

EVDPIAHLY

EVDPIGALY

EVDPIGHAY

EVDPIGHLA
```

The native and alanine-substituted peptides were pulsed on to antigen presenting cells, and interferon γ (IFNγ) production, as measured using the ELISpot assay, used as a read-out for T cell activation. Essential positions were defined by a greater than 50% reduction in T cell activity relative to the native peptide.

1.1a) Activation of a3a T Cells by Alanine-Substituted Peptides

ELISpot assays were carried out according to the manufacturer's instructions (BD BioSciences). HLA-A1+ hepatocyte cells were used as target cells and pulsed with 10 μM of each peptide. Target cells were counted and plated at 50,000 cells per well in 50 μl assay buffer (10% FCS, 88% RPMI 1640, 1% glutamine and 1% penicillin/streptomycin). Effector T cells used in this method were a 1:1 mix of CD4+ and CD8+ T cells (obtained by negative selection (using the CD4 and CD8 Negative Isolation Kits, Dynal) from peripheral blood lymphocytes (PBL) obtained from a healthy donor). Cells were stimulated with anti CD3/CD28 coated beads (T cell expander, Invitrogen), transduced with lentivirus carrying the gene encoding a3a T cell receptor, and expanded in assay media containing 50 U/ml IL-2 until between 10 and 13 days post transduction. Effector T cells were plated at 15,000 cells per well. Plates were incubated overnight at 37° C./5% $CO_2$ and quantified, after development, using an automated ELISpot reader (Immunospot Series 5 Analyzer, Cellular Technology Ltd.). Non-transduced PBLs from the same healthy donor were used as a negative control. All experiments were carried out in triplicate.

FIG. 1 shows IFNγ production by a3a transduced T cells in response to native (wt) MAGE A3 peptide and each alanine-substituted peptide. Five of the alanine-substituted peptides resulted in a greater than 50% decrease in IFNγ production compared to native MAGE A3 peptide. The corresponding native residue at each of these five positions may comprise the binding motif. In this case the binding motif is defined as EXDPIXXXY, where X is any amino acid.

1.1b) Activation of IMCmage1 Redirected T Cells by Alanine-Substituted Peptides

ELISpot assays were carried out as described in section (1.1a), except effector cells were prepared from peripheral blood mononuclear cells (PBMCs) blood using standard procedures utilising Lymphoprep (Axis-Shields, cat #NYC-1114547) and Leucosep tubes (Greiner, cat #227290), and plated at 25,000 cells per well. IMCmage1 was added to a final concentration of 0.1 nM per well. Controls were carried out in the absence of IMCmage1 (effectors+targets+peptide); and in the absence of peptide-pulsed target cells (effectors+IMCmage1).

Figure 2:
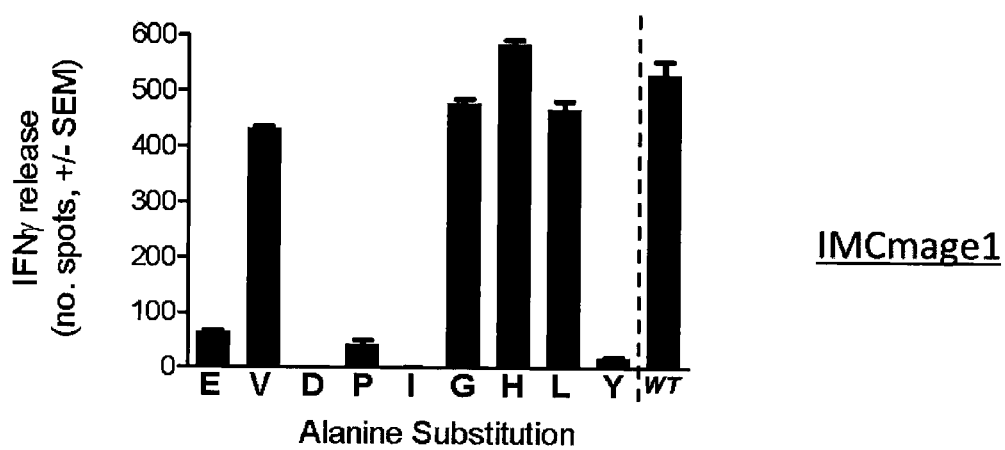
FIG. 2 shows IFNγ production by IMCmage1 redirected T cells in response to peptide-pulsed cells presenting either MAGE A3 peptide (denoted WT), or alanine-substituted peptides.

FIG. 2 shows IFNγ production by IMCmage1 redirected T cells in response to native (wt) MAGE A3 peptide and each alanine-substituted peptide. Five of the alanine-substituted peptides resulted in a greater than 50% decrease in IFNγ production compared to native MAGE A3. The corresponding native residue at each of these five positions may comprise the binding motif. In this case the binding motif is defined as EXDPIXXXY, where X is any amino acid.

1.1c) Activation of IMCmage1 Redirected T Cells by Glycine-Substituted Peptides

The same procedure was followed as detailed in section (1.1b) except the HLA-A*01+ hepatocyte target cells were pulsed with glycine-substituted peptides. MAGE A3 peptide contains one native glycine residue; in this case the native glycine was considered non-essential for the purposes of defining the motif.

Figure 3:
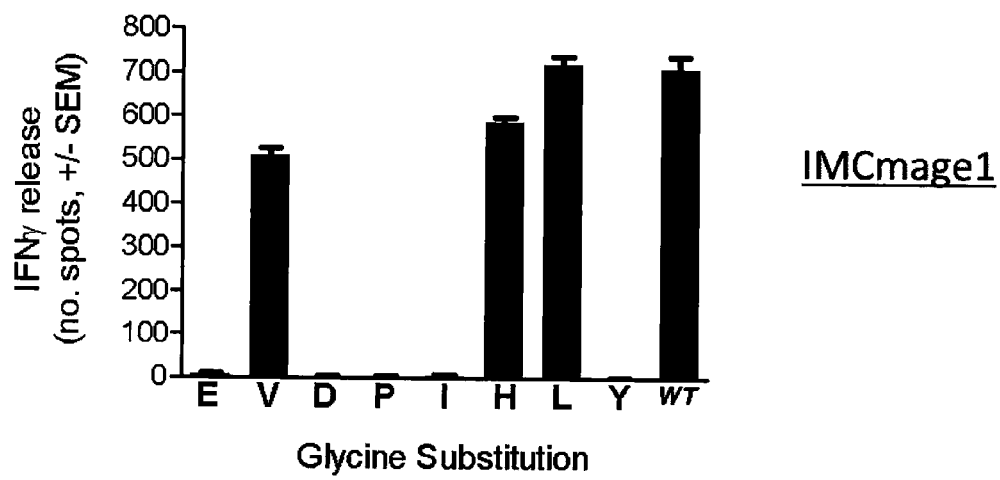
FIG. 3 shows IFNγ production by IMCmage1 redirected T cells in response to peptide-pulsed cells presenting either MAGE A3 peptide (denoted WT), or glycine-substituted peptides.

FIG. 3 shows IFNγ production by IMCmage1 redirected T cells in response to native (wt) MAGE A3 peptide and each glycine-substituted peptide. Five of the glycine-substituted peptides resulted in a greater than 50% decrease in IFNγ production compared to native MAGE A3. The corresponding native residue at each of these five positions may comprise the binding motif. In this case the binding motif is defined as EXDPIXXXY, where X is any amino acid.

1.2 Identification of Potential Off-Target Peptides

The ScanProsite tool (http://prosite.expasy.org/scanprosite) was used to search all UniProtKB/Swiss-Prot (release 2012_10 of 31 Oct. 12: 538259 entries) database sequences, for proteins which contain the motif identified above (entered as E-X-D-P-I-X-X-X-Y). No filters were used. Pattern options were set to allow at most 1 X sequence characters to match a conserved position in the pattern and the match mode was set to 'greedy, overlaps, no includes'.

Five unique human proteins were identified: native MAGE A3, MAGE family members A6 and B18, the muscle protein Titin, and a protein known as Dos. The amino acid sequences of the motif-containing peptides are shown in the table below (residues which may comprise the motif are underlined).

| Protein (Accession number) | Sequence | | | | | | | | |
|---|---|---|---|---|---|---|---|---|---|
| MAGE A3 (P43357) | <u>E</u> | V | <u>D</u> | <u>P</u> | <u>I</u> | G | H | L | <u>Y</u> |
| MAGE A6 (P43360) | <u>E</u> | V | <u>D</u> | <u>P</u> | <u>I</u> | G | H | V | <u>Y</u> |
| MAGE B18 (Q96M61) | <u>E</u> | V | <u>D</u> | <u>P</u> | <u>I</u> | R | H | Y | <u>Y</u> |
| Titin (Q8WZ42) | <u>E</u> | S | <u>D</u> | <u>P</u> | <u>I</u> | V | A | Q | <u>Y</u> |
| Dos (Q8N350) | <u>E</u> | P | <u>D</u> | <u>P</u> | <u>I</u> | L | D | N | <u>Y</u> |

The search results also identified a number of motif-containing peptides from common human pathogens. Two peptides were selected from the list as examples for further testing; a nuclease protein present in three strains of Epstein Barr Virus (EBV), and a ribosomal maturation factor from *Clostridium difficile*, the amino acid sequences of these peptides are shown below.

| Protein (Accession number) | Sequence | | | | | | | |
|---|---|---|---|---|---|---|---|---|
| EBV protein (Q1HVE7) (P03217) (Q3KSR5) | E | F | D | P | I | Y | P | S | Y |
| *C. difficile* protein (Q18BH3) | E | K | D | P | I | K | E | N | Y |

1.3 Confirming Cross Reactivity of Off Target Peptides

Potential off target peptides, identified above, were tested for their ability to cross react with a3a T cells and IMCmage1 redirected T cells using an IFNγ ELISpot assay.

1.3a) Testing for Activation of a3a T Cells by HLA-A*01+ Hepatocyte Cells Pulsed with Potential Off-Target Peptides All peptides were produced synthetically by Peptide Protein Research Limited, UK. Activation of a3a T cells was determined by IFNγ ELISpot assay using the same procedure as described in section 1.1a. HLA-A*01+ hepatocyte cells were used as targets and pulsed with 10 μM of each peptide. T cells were prepared from peripheral blood lymphocytes (PBLs) obtained from a healthy donor, and transduced with the a3a TCR. Non-transduced donor T cells were used as a negative control. T cell activation in response to cells pulsed with each of the motif-containing peptides was compared to activation by native MAGE A3 peptide pulsed cells.

Figure 4:
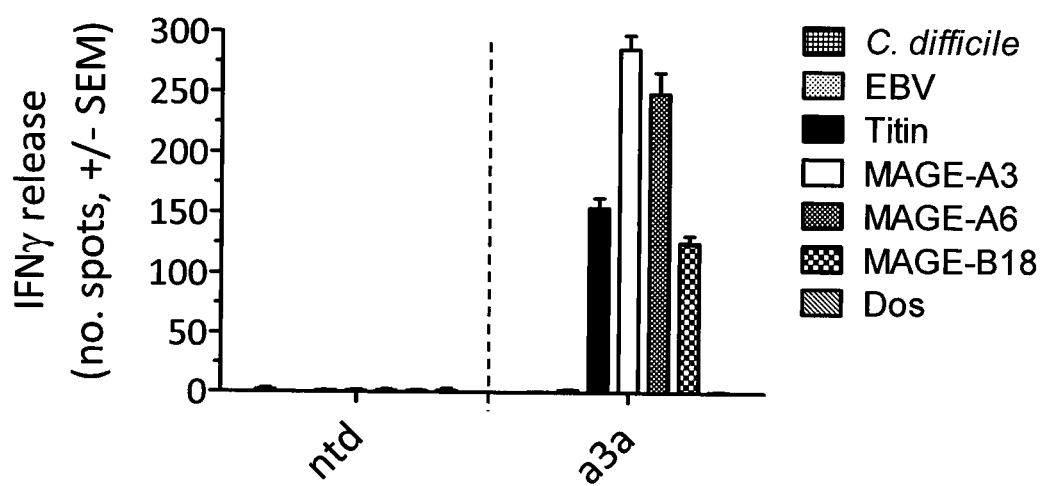
FIG. 4 shows IFNγ production by a3a T cells in response to cells pulsed with peptides identified in the motif search. Non-transduced T cells (ntd) were used as a negative control.

FIG. 4 shows that cells pulsed with MAGE A3, MAGE A6, MAGE B18 and Titin peptides led to activation of a3a T cells. Peptide Dos as well as peptides from EBV and *C. difficile* did not induce T cell activation.

1.3b) Testing for Activation of IMCmage1 Redirected T Cells by HLA-A*01+ Hepatocyte Cells Pulsed with Potential Off Target Peptides Peptide pulsed cells were prepared as described in 1.3a. Activation of IMCmage1 redirected T cells was determined by IFNγ ELISpot assay using the same procedure as described in section 1.1b.

Figure 5:
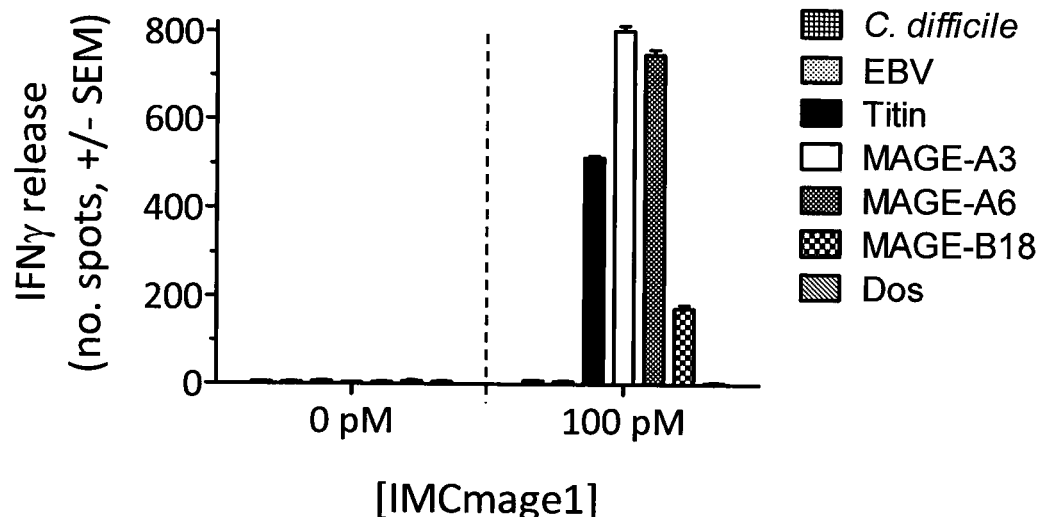
FIG. 5 shows IFNγ production by IMCmage1 redirected T cells in response to cells pulsed with peptides identified in the motif search. Experiments carried out in the absence of IMCmage1 were used as a negative control.

FIG. 5 shows that cells pulsed with MAGE A3, MAGE A6, MAGE B18 and Titin peptides led to activation of IMCmage1 redirected T cells. Peptide Dos as well as peptides from EBV and *C. difficile* did not induce T cell activation.

The experiments described in 1.3a and 1.3b confirm that there are three off target peptides which are bound by a3a T cells and IMCmage1 redirected T cells; MAGE A6, MAGE B18, and Titin. Of the three only Titin is relevant in a clinical context. Normal tissue expression of MAGE family proteins is restricted to male germ-line cells, whereas Titin is expressed in cardiac and skeletal muscle (Uniprot Protein Knowledgebase (http://www.uniprot.org/uniprot)).

1.3c) Measuring Affinity to T Cell Activating Peptides

Affinity was determined by surface plasmon resonance using a BIAcore 3000 instrument and reported in terms of an equilibrium dissociation constant ($K_D$). Soluble versions of the a3a and IMCmage1 TCRs were prepared using the method described in Boulter, et al., Protein Eng, 2003. 16: 707-711. Biotinylated specific and control pMHC monomers were prepared as described in Garboczi, et al. *Proc Natl Acad Sci USA* 1992. 89: 3429-3433 and O'Callaghan, et al., *Anal Biochem* 1999. 266: 9-15, and immobilized on to a streptavidin-coupled CM-5 sensor chip. All measurements were performed at 25° C. in PBS buffer (Sigma) supplemented with 0.005% Tween (Sigma) at a constant flow rate. To measure affinity, serial dilutions of the soluble TCRs were flowed over the immobilized pMHCs and the response values at equilibrium were determined for each concentration. Equilibrium dissociation constants ($K_D$) were determined by plotting the specific equilibrium binding against protein concentration followed by a least squares fit to the Langmuir binding equation, assuming a 1:1 interaction.

The results summarised in the table below confirm Titin peptide binds to soluble versions of the TCRs used in a3a T cells and IMCmage1. The affinity ($K_D$) is shown in the table below:

|  | MAGE-A3 (EVDPIGHLY) | MAGE-A6 (EVDPIGHVY) | MAGE-B18 (EVDPIRHYY) | Titin (ESDPIVAQY) |
| --- | --- | --- | --- | --- |
| IMCmage1 | 4.5 nM | 4.2 nM | 182 nM | 86 nM |
| MAGE a3a | ~2 µM | ~2 µM | ~100 µM | ~100 µM |

1.3d) Cytotoxicity of IMCmage1 Redirected T Cells to HLA-A*01+ Hepatocyte Cells Pulsed with Titin Peptide Killing assays were carried out using the IncuCyte FLR-Platform (Essen Biosciences). Flat bottomed 96 well plates were used for assay. The assay medium was RPMI (w/o phenol red+10% FCS+1% Pen/strep+1% Glu). HLA-A*01+ hepatocyte cells were plated at 10,000 cells per well and incubated overnight to allow them to adhere. Peptides were made up at 10 µM final concentration and added at 25 µl (60 µM) per well. Effector T cells (prepared as described in 1.1b) were thawed from liquid N2, counted and plated at 100,000/well. IMCmage1 was added to a final concentration of 1 nM. Control measurements were carried out in the absence of IMCmage1 (effectors+targets). Images were taken every 2 h, over a three day period, and the number of apoptotic cells per mm$^2$ was quantified using the CellPlayer 96-well Kinetic Caspase 3/7 reagent and the IncuCyte FLR-Platform. The reagent is cleaved by activated Caspase 3/7 upon target cell apoptosis resulting in the release of the dye and green fluorescent staining of nuclear DNA.

Figure 6:
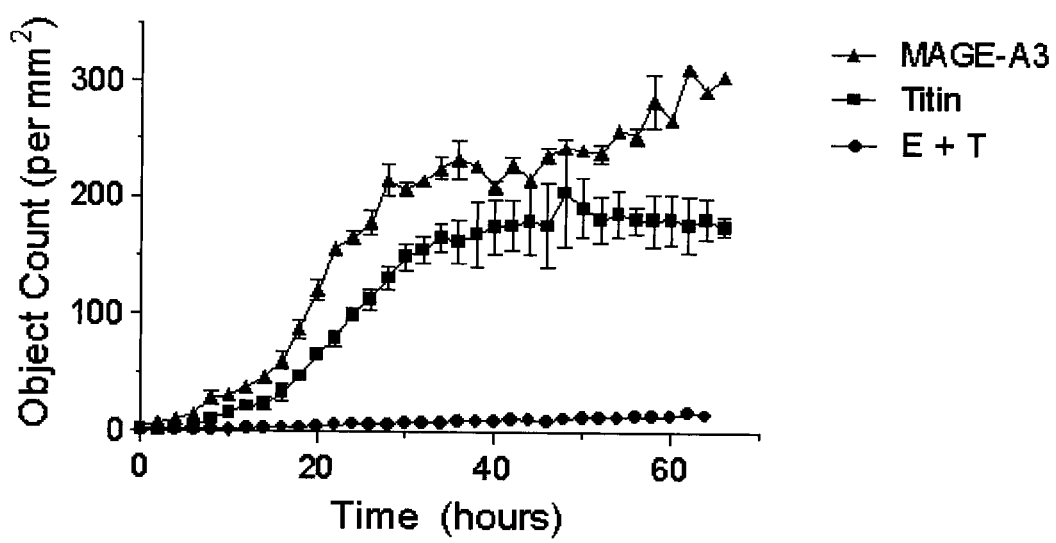
FIG. 6 shows IMCmage1 redirected T cell killing of cells pulsed with either MAGE A3 or Titin peptides. Cell killing was determined using the IncuCyte platform. A negative control was carried out using in the absence of IMCmage1 (E+T).

FIG. 6 shows IMCmage1 redirected T cells kill cells pulsed with Titin peptide to a similar degree as native MAGE A3.

1.3e) Activation of a3a T Cells by Cells Naturally Presenting Titin Peptide iCell cardiomyocytes were obtained from Cellular Dynamics International. iCell cardiomyocytes are highly purified human cardiomyocytes derived from induced pluripotent stem (iPS) cells and are electrically active with typical mechanical characteristics of cardiac tissue. These cells are positive for Titin and negative for MAGE A3 as determined by standard RT-PCR methods.

iCell cardiomyocytes were revived from liquid nitrogen and plated at 50,000 cells per well four days prior to the assay and treated as per the manufacturer's instructions. The iCell cardiomyocytes were virally transduced with HLA-A*01. EJM and colo205 (positive and negative controls respectively) were plated at 50,000 cells per well on the day of assay. iCell cardiomyocytes were washed once with R10 (RPMI+10% FCS+1% Pen/strep+1% Glu) and then incubated in R10 for the assay. a3a transduced T cells and corresponding non-transduced cells were taken from culture and plated at 50,000 cells per well. The cells were cultured for 24 h and then centrifuged at 800×g for 4 min, 100 ul of supernatant was then removed and placed in a clean plate. The plates were stored at −70° C. until thawing and developing to measure multiple cytokine release (IFNγ, GM-CSF and MIP-1β) by Luminex (25-plex kit), in accordance with manufacturer's instructions.

Figure 7:
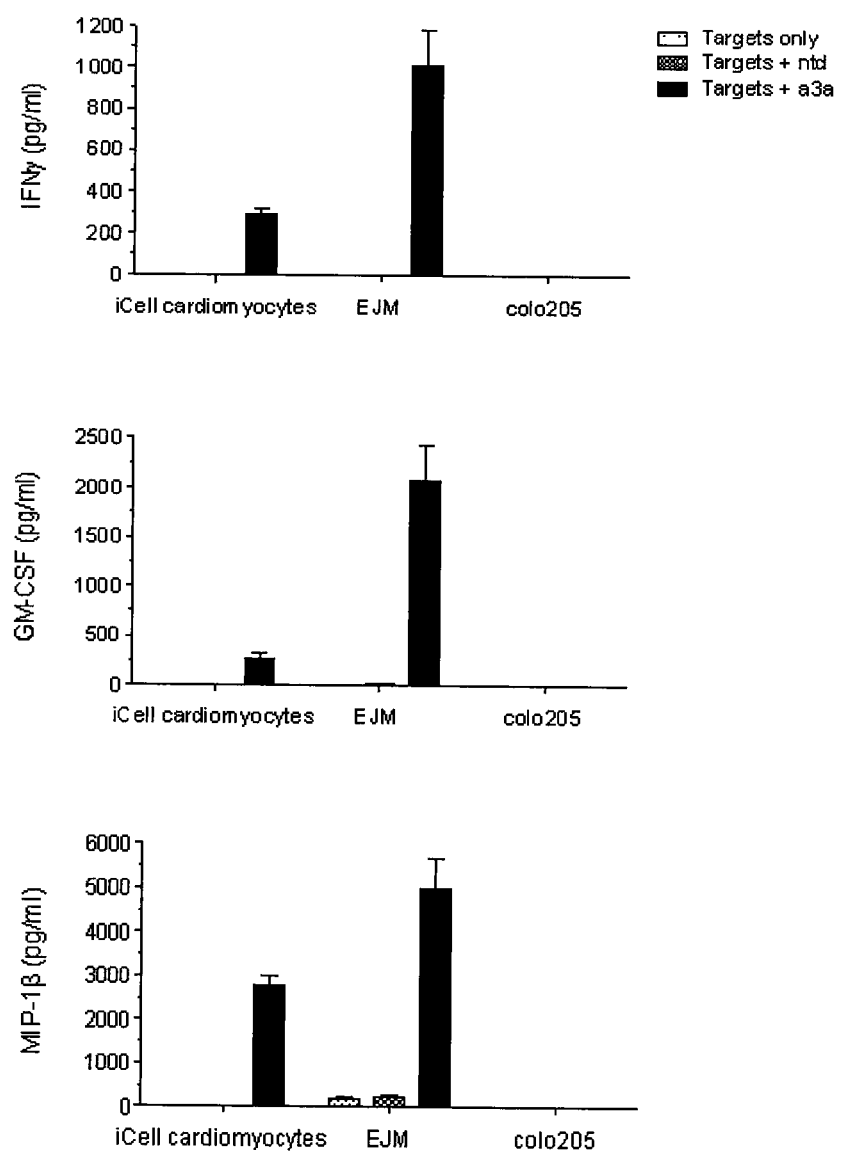
FIG. 7 shows the cytokine profile a3a T cells in the presence of iCells, as determined by the Luminex assay. EJM and colo205 cells were used as a positive and negative control respectively.

FIG. 7 shows a3a T cells release IFNγ, GM-CSF and MIP-1β in response to iCell cardiomyocytes.

1.3f) Killing of Cells Naturally Presenting Titin Peptide by a3a T Cells

Figure 8:
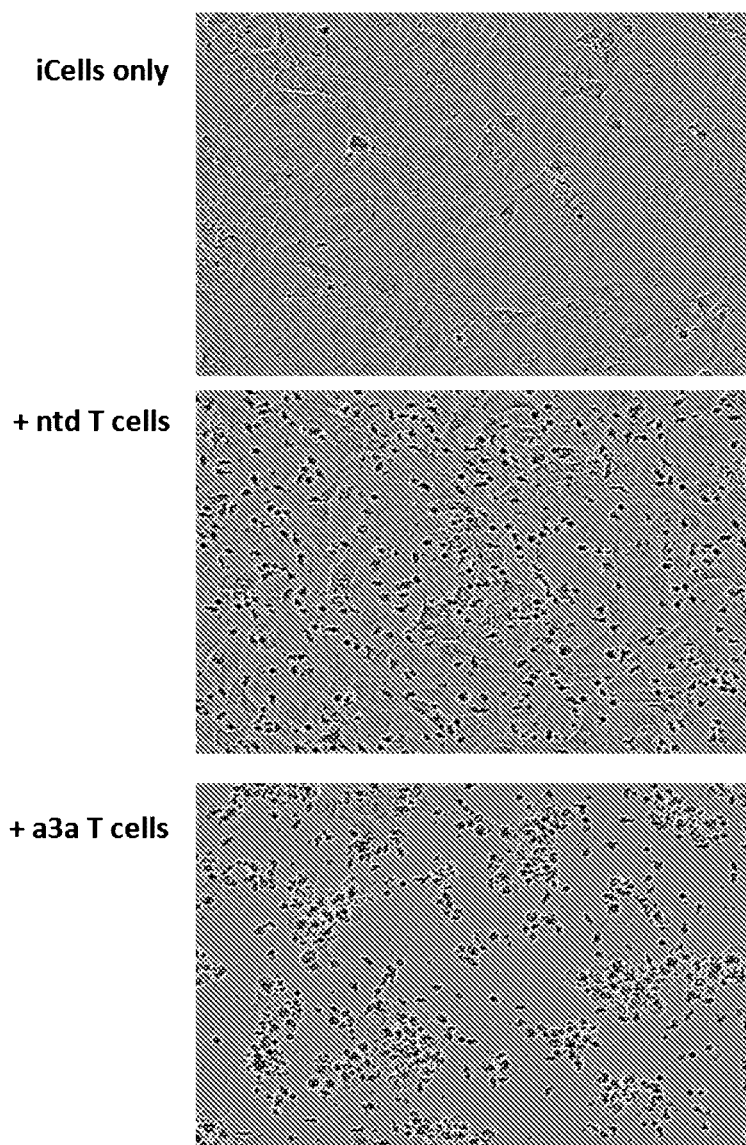
FIG. 8 shows phase contrast images, obtained using the IncuCyte platform, of Titin positive iCells being killed by a3a T cells. The images were taken after 24 hours incubation. Non-transduced T cells (ntd) were used as a negative control.

Phase contrast images were obtained after 24 h on the the IncuCyte FLR-Platform (Essen Biosciences), using the same experimental set-up as that described above (1.3e). FIG. 8 shows the resulting images obtained. In the presence of a3a T cells, iCells are destroyed.

Comparative Example 1

The following experiments show how the methods currently available in art do not, or would not, identify Titin as an off target peptide. These methods were not able to predict unwanted side effects when a3a T cells were administered to patients (manuscript in preparation).

a) Similarity Search

The RefSeq database was searched for human peptides with a similar sequence to MAGE A3, using protein BLAST (Basic Local Alignment Search Tool) version 2.2.27 (Altschul, et al, *Nucleic Acids Res.* 1997 25:3389-3402, http://blast.ncbi.nlm.nih.gov/Blast.cgi?CMD=Web&PAGE_TYPE=BlastHome). Algorithm parameters were adjusted automatically for a short protein. (General parameters; expect threshold=200000, word size=2: Scoring parameters; matrix=PAM30, gap costs=existence 9 extension 1; no compositional adjustments.)

The BLAST search returned over 100 hits, including MAGE A3, MAGE A6, and MAGE B18, but not Titin. 15 sequences were selected for testing using peptide pulsed targets (HLA-A*01+ hepatocyte cells) and IFNγ ELISpot assays as described in Example 1 (section 1.1a and 1.1b). The peptide sequences are detailed in FIG. 9. None of these peptides was able to activate a3a T cells or IMCmage1 redirected T cells.

b) Primary Cell Screening

HLA-A*01+ human cells from various tissues were screened for their ability to induce activation of a3a T cells and IMCmage1 redirected T cells. T cell activation was assessed by IFNγ release using an ELISpot assay as described in Example 1 (section 1.1a and 1.1b). Multiple lots were used for most primary cell types. Cells were grown in 2D culture.

Astrocytes
Cardiac Myocytes
Non-pigmented ciliary epithelial cells

Bronchial smooth muscle cells
Dermal fibroblasts
Dermal microvascular endothelial cells
Hepatocytes
Pulmonary Fibroblasts
Renal Epithelial Cells
Melanocytes
Skeletal Muscle
Pulmonary microvascular endothelial cells Results showed no obvious reactivity for IMCmage1 and a3a transduced T cells. Since expression of MAGE family proteins is restricted to male germ line cells, cross reactivity with MAGE A6 and MAGE B 18 is not detected. However, despite Titin being expressed in cardiac and skeletal muscle, this experiment failed to detect cross reactivity with skeletal and muscle cells. Since titin expression is known to be upregulated in differentiated tissue (Van der Loop, et al. (1996). J Muscle Res Cell Motil. 17:23-36), detecting cross reactivity required more specialised cell cultures (such as the iCells shown above).

c) Would a Mouse Model have Identified Off-Target Toxici

Sequence alignment of the full length human Titin protein with the mouse Titin protein was carried out using the align function on the Uniprot knowledgebase (http://www.uniprot.org/align). The equivalent mouse Titin peptide has the following sequence:

| Peptide | Peptide Sequence | | | | | | | |
|---|---|---|---|---|---|---|---|---|
| Titin - human | E | S | D | P | I | V | A | Q | Y |
| Titin - mouse | E | S | E | P | V | V | A | Q | Y |

Activation of a3a T cells was assessed using HLA-A*01+ hepatocyte cells pulsed with MAGE A3, human Titin or mouse Titin peptides. T cell activation was determined by IFNγ ELISpot assay as described above. Synthetic peptides were obtained from Peptide Protein Research Limited, UK.

FIG. 10 shows IFNγ release in response to HLA-A*01+ hepatocyte cells pulsed with MAGE A3 and human Titin; no IFNγ was detected when cells were pulsed with the equivalent Titin peptide from mouse. Therefore, a mouse model would not have identified Titin as an off target peptide leading to unwanted side effects when administered to a patient.

Example 2

The target MHC-presented peptide used in this example is derived from human cancer testis antigen NY-ESO-1 and has the following amino acid sequence; SLLMWITQC. NY-ESO-1 peptide is presented on antigen presenting cells in the context of HLA-A*02.

The binding peptide used in this example may comprise a modified T cell receptor (TCR) fusion protein which has been engineered to possess enhanced affinity for NY-ESO-1 peptide, and is termed ImmTAC-NYESO in this example. Production of such fusion proteins is described in McCormack et al, 2013, Cancer Immunol Immunother, 62 (4):773-85 and Liddy et al, 2012, Nat Med, 8:980-987.

2.1 Identification of the Binding Motif by Substitution with alanine

Variants of the native NY-ESO-1 peptide were obtained in which each amino acid position was sequentially replaced with alanine, as shown below (in each case the alanine substitution is underlined). Peptides were obtained from Peptide Protein Research Limited, UK.

ALLMWITQC

SALMWITQC

SLAMWITQC

SLLAWITQC

SLLMAITQC

SLLMWATQC

SLLMWIAQC

SLLMWITAC

SLLMWITQA

The native and alanine-substituted peptides were pulsed on to antigen presenting cells, and interferon γ (IFNγ) production, as measured using the ELISpot assay, used as a read-out for T cell activation. Essential positions were defined by a greater than 50% reduction in T cell activity relative to the native peptide.

ELISpot assays were carried as described in Example 1 section 1.1b except that HLA-A2+ T2 cells were used as target cells and effector PBMCs were plated at 40,000 cells per well. ImmTAC-NYESO was added to a final concentration of 0.1 nM per well.

Figure 11:
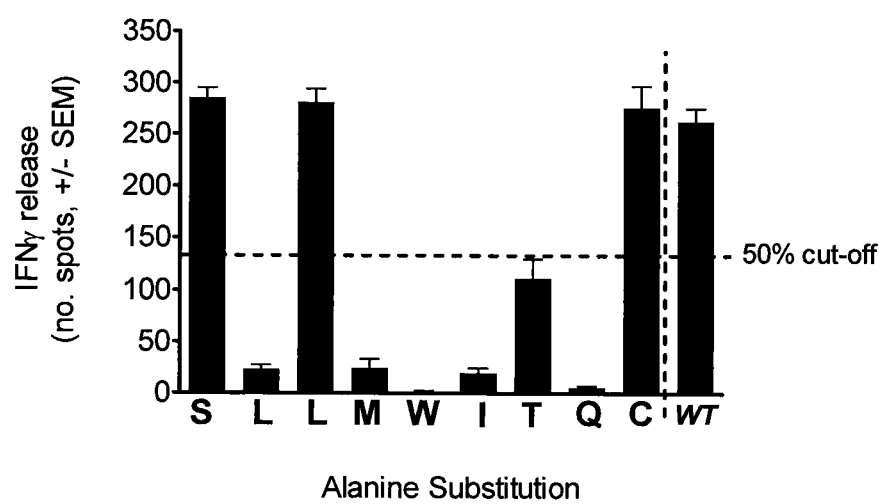
FIG. 11 shows IFNγ production by ImmTAC-NYESO redirected T cells in response to peptide-pulsed cells presenting either NY-ESO-1 peptide (denoted WT), or alanine-substituted peptides.

FIG. 11 shows IFNγ production by ImmTAC-NYESO redirected T cells in response to native (wt) NY-ESO-1 peptide and each alanine-substituted peptide. Five of the alanine-substituted peptides resulted in a greater than 50% decrease in IFNγ production compared to native NY-ESO-1 peptide. The corresponding native residue at each of these five positions may comprise the binding motif. In this case the binding motif is defined as XLXMWITQX, where X is any amino acid.

2.2 Identification of Potential Off-Target Peptides

The ScanProsite tool (http://prosite.expasy.org/scanprosite) was used to search the UniProtKB/Swiss-Prot database (release date 13 Nov. 2013) for proteins which contain the motif identified above (entered as X L X M W I T Q X). The search was limited to human sequences.

Two unique human proteins were identified, NY-ESO-1 (accession no: P78358) and LAGE-1A (accession no: O75638-2) an alternative cancer testis antigen possessing the same 9 amino acid sequence as the NY-ESO-1 peptide. TCRs that bind to the NY-ESO-1 peptide are known to recognise cancer cells expressing LAGE-A1 (McCormack et al, 2013, Cancer Immunol Immunother, 62 (4):773-85).

2.3 Identification of the Binding Motif by Substitution with all Alternative Amino Acids Variants of the native NY-ESO peptide were obtained in which the amino acid residue at each position was sequentially replaced with all 19 alternative naturally-occurring amino acids, such that 171 peptides were prepared in total. The native and amino-acid substituted peptides were pulsed on to antigen presenting cells, and interferon γ (IFNγ) production, as measured using the ELISpot assay, used as a read-out for T cell activation. Essential positions were defined by a greater than 50% reduction in T cell activity relative to the native peptide.

ELISpot assays were carried as described in section 2.1a.

Figure 12:
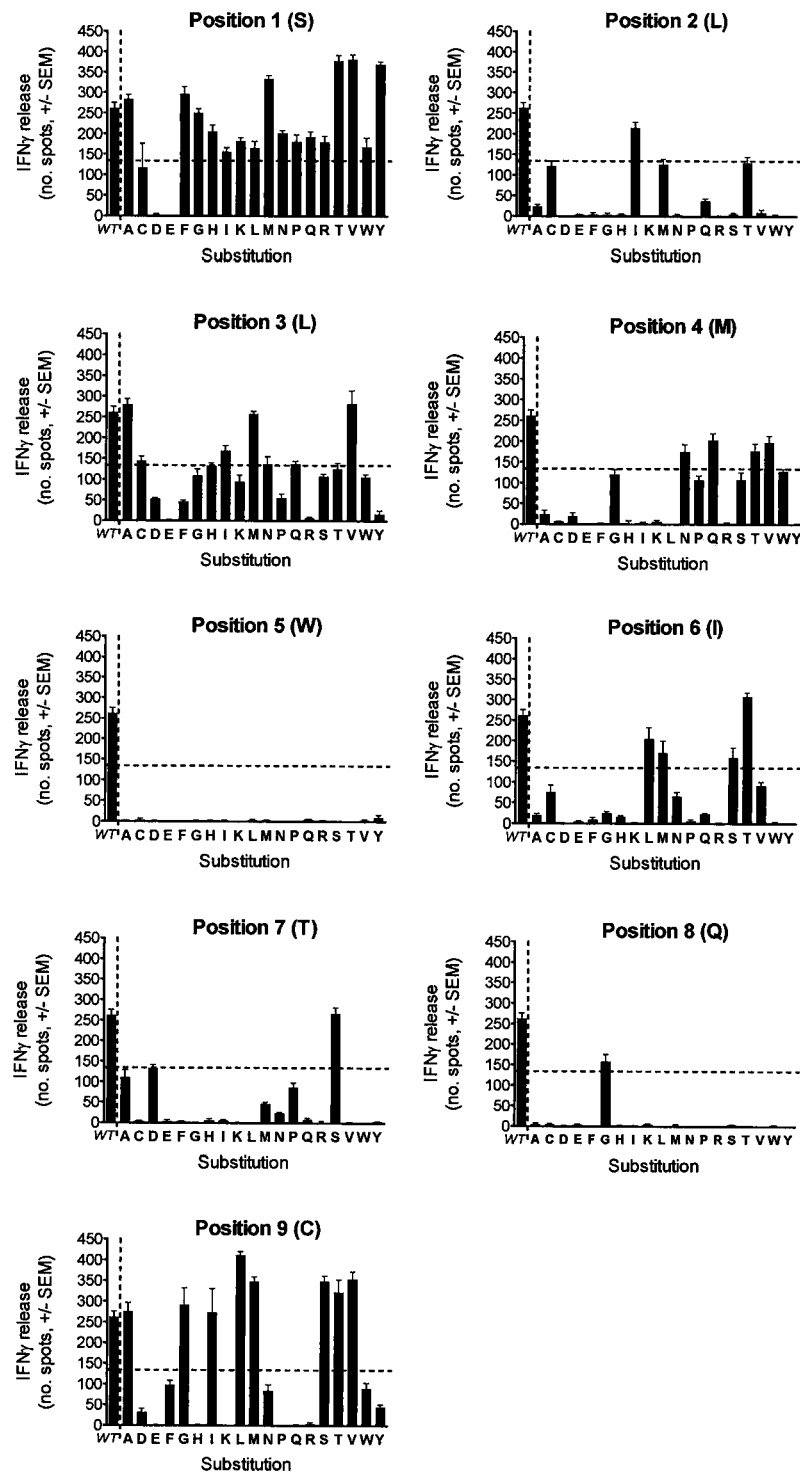
FIG. 12 shows IFNγ production by ImmTAC-NYESO redirected T cells in response to native (WT) NY-ESO-1 peptide and each amino-acid-substituted peptide.

FIG. 12 shows IFNγ production by ImmTAC-NYESO redirected T cells in response to native (wt) NY-ESO-1 peptide and each amino-acid-substituted peptide.

The tolerated residues at each position of the peptide are shown below. For each position the first tolerated residue shown corresponds to the native (WT) residue at that position.

| Position | Tolerated residues |
|---|---|
| 1 | S V T Y M F A G H N Q K P R W L I |
| 2 | L I |
| 3 | L V A M I C Q N H |
| 4 | M Q V T N |
| 5 | W |
| 6 | I T L M S |
| 7 | T S D |
| 8 | Q G |
| 9 | C L V M S T G A I |

2.4 Identification of Potential Off-Target Peptides

The ScanProsite tool was used as described in section 2.2, to search for proteins containing the tolerated residues at the indicated positions (entered as [SVTYMF-AGHNQKPRWLI]-[LI]-[LVAMICQNHHMQVTN]-W-[ITLMS]-[TSD]-[QG]-[CLVMSTGAI])

Two unique proteins were found (exincluding NY-ESO and LAGE A1).

| Protein (accession number) | Peptide sequence | Position |
|---|---|---|
| Plexin-D1 (Q9Y4D7) | HLCMWSDGC | 867-875: |
| von Willebrand factor A domain-containing protein 5B1 (Q5TIE3) | GLLNWITGA | 3-11 |

Peptides from Plexin-D1 and protein 5B1 are tested in vitro as described in Example 1.3, to confirm recognition by ImmTAC-NYESO. The potential of these off-target peptides to cause unwanted side effects in vivo is determined by, for example, reference to literature sources detailing expression of Plexin-D1 and protein 5B1 in normal tissue. Where expression in normal tissue is widespread, or in critical tissues, binding of ImmTAC-NYESO may additionally be confirmed in vitro using cells which express the off target peptide.

Comparative Example 2 a) Similarity Search

A similarity search was performed on the WT sequence of the NY-ESO-1 peptide using the BLAST tool as described in Comparative Example 1a. The top 100 hits did not return either of the two motif containing peptides identified above.

b) Comparison with Peptides from Homologous Proteins in Mouse

Sequence alignment of the full length human Plexin D1 and 5B1 proteins with the homologous protein from mouse (accession no: NP_080652.2 and NP_083677.1, respectively) was carried out using the align function on the Uniprot knowledgebase (http://www.uniprot.org/align). Comparison of the respective peptide sequences is shown below:

| Peptide | Peptide Sequence | | | | | | | |
|---|---|---|---|---|---|---|---|---|
| Plexin D1 - human | H | L | C | M | W | S | D | G | C |
| Plexin D1 - mouse | H | L | C | M | W | N | D | G | C |

| Peptide | Peptide Sequence | | | | | | | |
|---|---|---|---|---|---|---|---|---|
| Protein 5B1 - human | G | L | L | N | W | I | T | G | A |
| Protein 5B1 - mouse | G | L | L | N | C | L | T | G | A |

Neither of the mouse peptides contains the motif identified in section 2.3, therefore a mouse model may not identify potential cross reactivity.

The invention is further described by the following numbered paragraphs:

1. A method for predicting whether a binding peptide, which binds to a target peptide presented by a Major Histocompatibility Complex (MHC) and is for administration to a subject, has the potential to cross react with another peptide in the subject in vivo, the method comprising:
   identifying at least one binding motif in the target peptide to which the binding peptide binds; and
   searching for peptides that are present in the subject that comprise the at least one binding motif and that are not the target peptide,
   wherein the presence of one or more such peptides indicates that the binding peptide has the potential to cross react in vivo.

2. The method of paragraph 1, wherein the at least one binding motif is identified by:
   creating a series of mutants of the target peptide, each mutant having the amino acid residue at one position in the binding sequence thereof that is involved in binding to the binding peptide substituted for an alternative amino acid, such that over the series of mutants the amino acid residue in each position in the binding sequence is substituted for an alternative amino acid; and
   testing each mutant in the series for its activity relative to the wild type target peptide,
   wherein an amino acid residue at a position within the binding sequence is identified as being part of the binding motif if the mutant in which the amino acid at that position is mutated to an alternative amino acid has a substantial loss of activity relative to the wild type target peptide.

3. The method of paragraph 2, further comprising, where an amino acid residue at a position in the binding sequence is not identified as being part of the binding motif, substituting this position with at least one additional amino acid and testing for activity relative to the wild type peptide,
   wherein amino acid substitutions which result in a substantial loss of activity relative to the wild type target peptide are considered to be non-tolerated amino acids and not part of the binding motif and/or amino acid substitutions which do not result in a substantial loss of activity relative to the wild type target peptide are considered as part of the binding motif.

4. The method of paragraph 2 or paragraph 3, further comprising creating a series of mutants, each mutant having the amino acid residue at one position in the binding sequence substituted for an alternative amino acid, such that over the series of mutants the amino acid residue in each position in the binding sequence is substituted for all alternative amino acids, and testing each mutant in the series for activity relative to the wild type peptide,
   wherein amino acid substitutions which result in a substantial loss of activity relative to the wild type target peptide are considered to be non-tolerated amino acids and not part of the binding motif and/or amino acids substitutions which do not result in a substantial loss of activity relative to the wild type target peptide are considered as part of the binding motif.

5. The method of paragraph 2, 3 or 4, wherein the activity that is tested is the ability of the mutant to bind to the binding peptide and/or to elicit the biological response caused by binding to the binding peptide.

6. The method of any one of paragraphs 2 to 5, wherein the alternative amino acid has a different side chain to that of the amino acid for which it is being substituted.

7. The method of any one of paragraphs 2 to 6, wherein the alternative amino acid is one that does not appear in the sequence that is involved in binding to the target peptide.

8. The method of paragraph 7, wherein the alternative amino acid is alanine or glycine.

9. The method of any preceding paragraph, wherein the subject is a human and the search is carried out for peptides that are of human origin or of organisms which are commonly present in humans.

10. The method of any preceding paragraph, wherein the search is carried out for peptides that are expressed in selected tissue(s) and/or accessible to the binding peptide.

11. The method of any preceding paragraph, further comprising testing binding to the target peptide of any peptide that is present in the subject that comprises the at least one binding motif.

12. The method of any preceding paragraph, further comprising, if no peptides that are present in the subject that comprise the at least one binding motif are found, using the binding peptide for preventing or treating a disease or condition which is ameliorated by administration of the binding peptide.

13. The method of any preceding paragraph, wherein the binding peptide is an immune binding peptide.

14. The method of paragraph 11, wherein the immune binding peptide is a T cell receptor or an antibody.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for selecting for administration to a subject a binding peptide which binds to a wild type target peptide presented by a Major Histocompatibility Complex (MHC) and that does not have the potential to cross react with another peptide in the subject in vivo so as to cause unwanted side effects, the method comprising:
   (a) identifying at least one binding motif in the wild type target peptide to which the binding peptide binds;
   (b) searching for peptides that are present in the subject that comprise the at least one binding motif and that are not the wild type target peptide;
   (c) testing binding of any such peptide to the binding peptide in vitro,
      wherein the presence of one or more such peptides that bind to the binding peptide predicts that the binding peptide has the potential to cross react in vivo, and (d) selecting for administration a binding peptide that binds to the wild type target peptide presented by MHC and that is predicted not to have the potential to cross react with another peptide in the subject in vivo so as to cause unwanted side effects, wherein the identifying at least one binding motif in step (a) comprises:

a(i) creating a series of mutants of the wild type target peptide, each mutant having an amino acid residue at one position in the binding sequence thereof that is involved in binding to the binding peptide substituted for an alternative amino acid, such that over the series of mutants the amino acid residue in each position in the binding sequence is substituted for an alternative amino acid; and testing each mutant in the series for its activity relative to the wild type target peptide, wherein an amino acid residue at a position within the binding sequence is identified as being part of the binding motif if the mutant in which the amino acid at that position is mutated to the alternative amino acid has a 50% or greater loss of activity relative to the wild type target peptide, or a(ii) creating a series of mutants, each mutant having an amino acid residue at one position in the binding sequence substituted for an alternative amino acid, such that over the series of mutants the amino acid residue in each position in the binding sequence is substituted for all alternative amino acids; and testing each mutant in the series for activity relative to the wild type peptide, wherein amino acid substitutions which result in a 50% or greater loss of activity relative to the wild type target peptide are considered to be non-tolerated amino acids and not part of the binding motif and/or amino acids substitutions which do not result in a 50% or greater loss of activity relative to the wild type target peptide are considered as part of the binding motif.

2. The method of claim 1, further comprising, in step 1(a)(i), where an amino acid residue at a position in the binding sequence is not identified as being part of the binding motif, substituting this position with at least one additional amino acid and testing for activity relative to the wild type peptide, wherein amino acid substitutions which result in a 50% or greater loss of activity relative to the wild type target peptide are considered to be non-tolerated amino acids and not part of the binding motif and/or amino acid substitutions which do not result in a 50% or greater loss of activity relative to the wild type target peptide are considered as part of the binding motif.

3. The method of claim 1, wherein the activity that is tested is the ability of the mutant to bind to the binding peptide and/or to elicit the biological response caused by binding to the binding peptide.

4. The method of claim 1, wherein the alternative amino acid has a different side chain to that of the amino acid for which it is being substituted.

5. The method of claim 1, wherein the alternative amino acid is one that does not appear in the sequence that is involved in binding to the wild type target peptide.

6. The method of claim 5, wherein the alternative amino acid is alanine or glycine.

7. The method of claim 1, wherein the subject is a human and the search is carried out for peptides that are of human origin or of organisms which are commonly present in humans.

8. The method of claim 1, wherein the search is carried out for peptides that are expressed in selected tissue(s) and/or accessible to the binding peptide.

9. The method of claim 1, further comprising, if no peptides that are present in the subject that comprise the at least one binding motif are found, using the binding peptide for preventing or treating a disease or condition which is ameliorated by administration of the binding peptide.

10. The method of claim 1, wherein the binding peptide is an immune binding peptide.

11. The method of claim 10, wherein the immune binding peptide is a T cell receptor or an antibody.

12. The method of claim 1, wherein the MEW is HLA class I or class II.

13. The method of claim 1, wherein step (d) further comprises, if a binding peptide is predicted to cross-react with another peptide in the subject in vivo, determining whether binding to the off target cross-reactive peptide has the potential to cause unwanted side effects.

* * * * *

UNITED STATES PATENT AND TRADEMARK OFFICE
CERTIFICATE OF CORRECTION

PATENT NO. : 11,017,882 B2  
APPLICATION NO. : 14/741828  
DATED : May 25, 2021  
INVENTOR(S) : Brian John Cameron et al.

Page 1 of 1

It is certified that error appears in the above-identified patent and that said Letters Patent is hereby corrected as shown below:

On the Title Page

Item (72), in Column 1, in "Inventors", Line 1, after "Abingdon" insert -- Oxfordshire --.

Item (72), in Column 1, in "Inventors", Line 2, after "Abingdon" insert -- Oxfordshire --.

Item (72), in Column 1, in "Inventors", Line 4, after "Abingdon" insert -- Oxfordshire --.

In the Claims

In Column 42, in Claim 12, Line 37, delete "MEW" and insert -- MHC --.

Signed and Sealed this  
Seventh Day of January, 2025

Derrick Brent  
*Acting Director of the United States Patent and Trademark Office*